US006913606B2

(12) United States Patent
Saitou et al.

(10) Patent No.: US 6,913,606 B2
(45) Date of Patent: Jul. 5, 2005

(54) HAIR REMOVING DEVICE WITH A LOTION APPLICATOR

(75) Inventors: Atsuhiro Saitou, Hikone (JP); Jyuzaemon Iwasaki, Nagahama (JP); Masakatsu Araki, Hikone (JP); Hideki Tanaka, Hikone (JP); Masanobu Yamasaki, Hikone (JP); Hirokazu Katou, Hikone (JP)

(73) Assignee: Matsushita Electric Works, Ltd., Kadoma (JP)

(*) Notice: Subject to any disclaimer, the term of this patent is extended or adjusted under 35 U.S.C. 154(b) by 246 days.

(21) Appl. No.: 10/131,195

(22) Filed: Apr. 25, 2002

(65) Prior Publication Data

US 2002/0161380 A1 Oct. 31, 2002

(30) Foreign Application Priority Data

Apr. 27, 2001 (JP) ....................................... 2001-133082
Jun. 14, 2001 (JP) ....................................... 2001-180805

(51) Int. Cl.[7] ................................................ A61B 17/50
(52) U.S. Cl. ........................................ 606/133; 606/131
(58) Field of Search ................................. 606/133, 131; 30/41.5, 41; 132/221, 289, 29 E; 417/391, 428; 239/127, 126

(56) References Cited

U.S. PATENT DOCUMENTS 3,090,119 A 5/1963 Jepson
3,176,392 A * 4/1965 Gwinn .......................... 30/41
5,092,041 A * 3/1992 Podolsky ........................ 30/41
5,337,478 A * 8/1994 Cohen et al. ................ 30/41.5
6,126,669 A 10/2000 Rijken et al.
6,312,436 B1 * 11/2001 Rijken et al. ............... 606/133
6,594,905 B2 * 7/2003 Furst et al. ..................... 30/41

FOREIGN PATENT DOCUMENTS

| | | |
|---|---|---|
| DE | 199 07 222 | 8/2000 |
| JP | 59108874 | 7/1984 |
| WO | WO 98/08661 | 3/1998 |
| WO | WO 00/48797 | 8/2000 |

* cited by examiner

*Primary Examiner*—Pedro Philogene
(74) *Attorney, Agent, or Firm*—Oblon, Spivak, McClelland, Maier & Neustadt, P.C.

(57) ABSTRACT

A hair removing device capable of feeding a lotion in association with a hair removing operation. The device has a treatment head that is mounted on a housing and includes a hair removing unit for hair depilation or hair epilation and an applicator for supplying a lotion on a user's skin. Also included in the device is a tank holding the lotion and a lotion supply mechanism for supplying the lotion from the tank to the applicator. The treatment head is formed with an actuator which acknowledges an even of the treatment head coming into an operative condition with the skin and activates a lotion supply mechanism to supply the lotion from the tank to the applicator when such event is acknowledged.

4 Claims, 30 Drawing Sheets

HAIR REMOVING DEVICE WITH A LOTION APPLICATOR

BACKGROUND OF THE INVENTION

1. Field of the Invention

The present invention is directed to a hair removing device with a lotion applicator, and more particularly to the personal hair removing device capable of feeding a lotion for facilitating the hair treatment as well as for making a skin care.

2. Description of the Prior Art

WO98/08661 and Japanese Utility Model Publication No. 59-108574 disclose a portable shaver capable of feeding a lotion for facilitating the shaving. The shaver incorporates a pump which is activated by a button or switch to feed the lotion over a user's skin where the shaving is intended. The button or switch is mounted on a shaver housing to be accessibly by a finger of the user grasping the housing, so that the user is required to manipulate the button or the switch each time the lotion feeding is desired. However, it is a normal shaving practice to move the shaver intermittently across the skin, i.e., moving from one portion to another portion of the skin through an action of releasing the shaver once from the skin. Thus, the user has to repeat turning on and ff the pump until finishing the shaving, otherwise the pump would be activated continuously to dispense the liquid wastefully.

DISCLOSURE OF THE INVENTION

In view of the above inconvenience, the present invention has been achieved to provide an improved hair removing device which is capable of feeding a lotion properly to an intended portion in association with the hair removing treatment, yet without requiring an additional switching operation. The device in accordance with the present invention includes a housing carrying a treatment head to be held against a user's skin. The treatment head includes a hair removing unit for hair depilation or hair epilation, and an applicator which dispenses a lotion on the user's skin. A lotion supply mechanism is provided to supply the lotion from a tank to the applicator. The treatment head is provided with an actuator which acknowledges an event of the treatment head coming into an operative condition with the skin and which activates the lotion supply mechanism to supply the lotion from the tank to the applicator when the event is acknowledged.

Thus, the applicator is enabled to dispense the lotion over the skin where the hair removing is made or being made without requiring an extra and cumbersome switching work to the user. That is, the user can enjoy the hair removing supplemented with the lotion, yet without being bothered to manipulate a particular switch or handle.

Preferably, the actuator is included in the applicator in a skin-contact relation with the skin and is movable relative to the housing so as to actuate the lotion supply mechanism when it is depressed as a result of the applicator being pressed against the user's skin. With this arrangement, the user is only required to bring the applicator in contact with the skin for feeding the lotion, making it possible to feed the lotion properly while making the hair removing, yet without being conscious of the actuator.

The applicator may be configured to include a header having a chamber for temporarily storing the lotion supplied from the tank. The header has at least one aperture which communicates with the chamber and is fifed with a rotating element such as a ball and a roller that defines the actuator. The rotating element is held rotatable in the aperture so as to come into rolling contact with the user's skin for applying the lotion over the skin. Thus, it is easy to feed the lotion smoothly over the skin with the aid of the rotating element.

The rotating element may be supported on a floating bed which is movable together with the rotating element within the header. In this connection, the lotion supply mechanism includes a stop valve formed in a flow path from the tank to the chamber. The floating bed is interlocked with the stop valve in order to open the stop valve only when the bed is depressed together with the rotating element. In this manner, the lotion can be supplied only when the rotating element is depressed such that the lotion supply can be stopped when the rotation element, i.e., the actuator is released from the user's skin, thereby avoiding the lotion from being dispensed while the device is away from the user's skin, without posing no additional action to the user. The rotating element may be made of an elastic material for soft and smooth contact with the skin.

In order to supply the lotion effectively from the tank to the chamber, the lotion supply mechanism is preferred to include a pressurizer which gives a positive pressure to the lotion in the tank, thus allowing the lotion to be supplied to the chamber under the pressure when the stop valve is opened.

Instead of providing the rotating element, the header of the applicator may carry a skin guide as the actuator which is adapted to come into contact with the user's skin. The skin guide has at least one aperture which communicates with the chamber for dispensing the lotion on the user's skin. The skin guide is floatingly supported to the header to be movable relative thereto and is interlocked with the stop valve so as to open the stop valve only when the skin guide is depressed as a result of the skin guide being pressed against the user's skin. The skin guide may be also made of an elastic material.

Further, the applicator itself may be floatingly supported to the housing so as to be depressed when pressed against the use's skin. This is advantageous in that the applicator can be easy to follow the contours of the user's skin for successfully applying the lotion while the treatment head is moving across the user's skin.

When the hair removing unit is configured to have an overall section which is wider towards its bottom than at its top end with respect to an upright axis of the unit, the applicator can be designed not to interfere with the removing unit while being kept in closely adjacent relation therewith. The applicator is movable relative to the housing between a projected position where the applicator has its top end closed to the top end of the hair removing unit and a retracted position where the applicator has its top end lowered from the top end of the hair removing unit. The applicator has a longitudinal axis along which it is movable relative to the housing. When the applicator is in the projected position, the longitudinal axis of the applicator is inclined at a first angle with respect to the upright axis of the hair removing unit so as to bring the top end of the applicator close to the top end of the hair removing unit. When the applicator is in the retraced position, the longitudinal axis of the applicator is inclined at a second angle different from the first angle with respect to the upright axis of the hair removing unit so as to avoid the applicator from interfering with the bottom of the hair removing unit.

In a preferred embodiment, the applicator, the tank and the lotion supply mechanism is integrated into a single module which is detachable to the housing. Thus, it is easy to refill the lotion as well as to clean the applicator. The single module may be floatingly supported to the housing.

Further, the lotion supply mechanism may include an electrically operated pump which draws the lotion from the tank and delivers it to the applicator. In this connection, the actuator may be realized by an electric switch projecting in proximity to the hair removing unit so as to be closed when it comes into contact with the user's skin. Thus, each time the switch is depressed, it will activate the pump to deliver the lotion to the applicator for feeding it over the skin.

When the hair removing unit includes a cassette which carries a hair removing element such as a cutting foil and which is floatingly supported to be housing to be capable of being depressed in response to the hair removing element being pressed against the user's skin, the actuator is interlocked with the cassette to activate the pump each time the cassette is depressed. Thus, the lotion is fed over the skin only as a consequence of the hair removing unit is pressed against the skin, thereby facilitating the hair and skin care while the user is unconscious of the lotion supply mechanism.

The device may include the actuator of another type which projects above the hair removing element for contact with the user's skin and is movable relative to the housing so as to be depressed when contacting with the user's skin. The actuator is interlocked to activate the pump for delivering the lotion to the applicator each time the actuator is depressed. Thus, the lotion can be applied as a consequence of the hair removing unit is pressed against the user's skin.

The hair removing unit may be configured to carry a pair of short-hair cutters and a long-hair trimmer each having a longitudinal axis perpendicular to an upright axis of the housing. The long-hair trimmer is interposed between the short-hair cutters with the individual longitudinal axes being held in parallel relation with each other. For the hair removing unit of this type, the applicator may be located between the long-hair trimmer and at least one of the short-hair cutters, or located outwardly of at least one of the short-hair cutters away from the long hair trimmer for dispensing the lotion effectively on the skin.

In a preferred embodiment where the applicator is floatingly supported to the housing to be movable relative thereto with respect to the upright axis of the housing, and also to the tank fixed to the housing with respect to the upright axis, the applicator is connected to the tank by way of a flexible tube so as to be supplied with the lotion from the tank. The flexible tube is therefore responsible for permitting the displacement of the applicator relative to the tank. The flexible tube may be deformable in its radial direction, or may be in the form of a bellows.

Further, the applicator may be latched at a lowered position where the applicator has its top retracted from the top end of the hair removing unit. Therefore, when the lotion feed is not required, the applicator can be kept away from the hair removing unit so as not to disturb the hair removing operation.

The lotion supply mechanism may include a pump having a pump chamber for temporarily storing the lotion supplied from the tank. The pump is designed to have an inlet flap valve permitting the lotion to be fed into the pump chamber from the tank and an outlet flap valve permitting the lotion to be delivered from the pump chamber to the applicator. The actuator, which moves to the depressed position against a bias, is interlocked with the pump such that only the outlet flap valve is caused to open for feeding the lotion to the applicator from the pump chamber in response to the actuator being depressed and that only the inlet flap valve is caused to open for drawing the lotion into the pump chamber from the tank in response to the actuator returning to a non-depressed position under the bias. Therefore, the pump is activated to repeat drawing the lotion from the tank and feeding it to the applicator as the actuator is pressed against the skin and released therefrom, thereby applying the lotion in synchronous with the movement of the treatment head.

In this connection, the pump is preferred to have the pump chamber which is surrounded by a stationary wall member with the inlet flap valve and a movable wall member with the outlet valve. The movable wall member is movable relative to the stationary wall member to vary a volume of the pump chamber. The actuator is interlocked with the movable wall member so as to generate a positive pressure within the pump chamber for feeding the lotion to the applicator through the outlet flap valve when the movable wall member moves towards the stationary wall member in response to the actuator moving to the depressed position. When the movable wall member moves away from the stationary wall member in response to the actuator returning to the non-depressed position, a negative pressure is developed in the pump chamber to draw the lotion into the pump chamber through the inlet flap valve. Thus, the lotion feed can be made simply by pressing and releasing the actuator against and from the skin, yet without relying on an additional driving source for the pump.

The actuator may be included in the applicator in the form of a skin guide for contact with the user's skin. The skin guide includes at least one aperture which communicates with the pump chamber through the outlet flap valve for dispensing the lotion over the skin.

Alternatively, the movable wall member serves itself as the skin guide that defines the actuator and also the applicator with the outlet flap valve. The skin guide is provided with a projection around the outlet flap valve in order to protect it from interfering with the user's skin. In addition to thus configured pump, the lotion supply mechanism may include a stop valve formed in the flow path from the tank to the pump. The stop valve is interlocked with the actuator, i.e., the skin guide so that it is opened only when the skin guide is depressed as a consequence of the projection being pressed against the user's skin, thereby giving a safe interruption of the lotion feed when it is not intended.

Further, the applicator may have a header which is fixed to the housing for temporarily storing the lotion supplied from the tank and include at least one lotion dispensing pipe extending on top of the hair removing unit. The pipe is floatingly supported to the header to be capable of being depressed together with the hair removing unit. In this version, the lotion supply mechanism includes a stop valve formed in the flow path from the tank to the header and also includes a pressurizer which gives a positive pressure to the lotion in the tank for allowing the lotion to be supplied to the header under the positive pressure. The stop valve is interlocked with the hair removing unit so as to open only when the hair removing unit is depressed, thereby dispensing the lotion supplied from the tank through the pipe depressed together with the hair removing unit in synchronize with the hair removing unit being depressed.

In this connection, the applicator may include a bar which is incorporated in the hair removing unit and is exposed on top of the hair removing unit for contact with the user's skin. The bar is introduced to detachably hold a plurality of the lotion dispensing pipes and serves as the actuator or the skin guide which activates to open the stop valve upon the bar being pressed against the user's skin.

These and still other objects and advantageous features of the present invention will become more apparent from the following description of the preferred embodiments when taken in conjunction with the attached drawings.

DETAILED DESCRIPTION OF THE PREFERRED EMBODIMENTS

First Embodiment <FIGS. 1 to 10>

Figure 1:
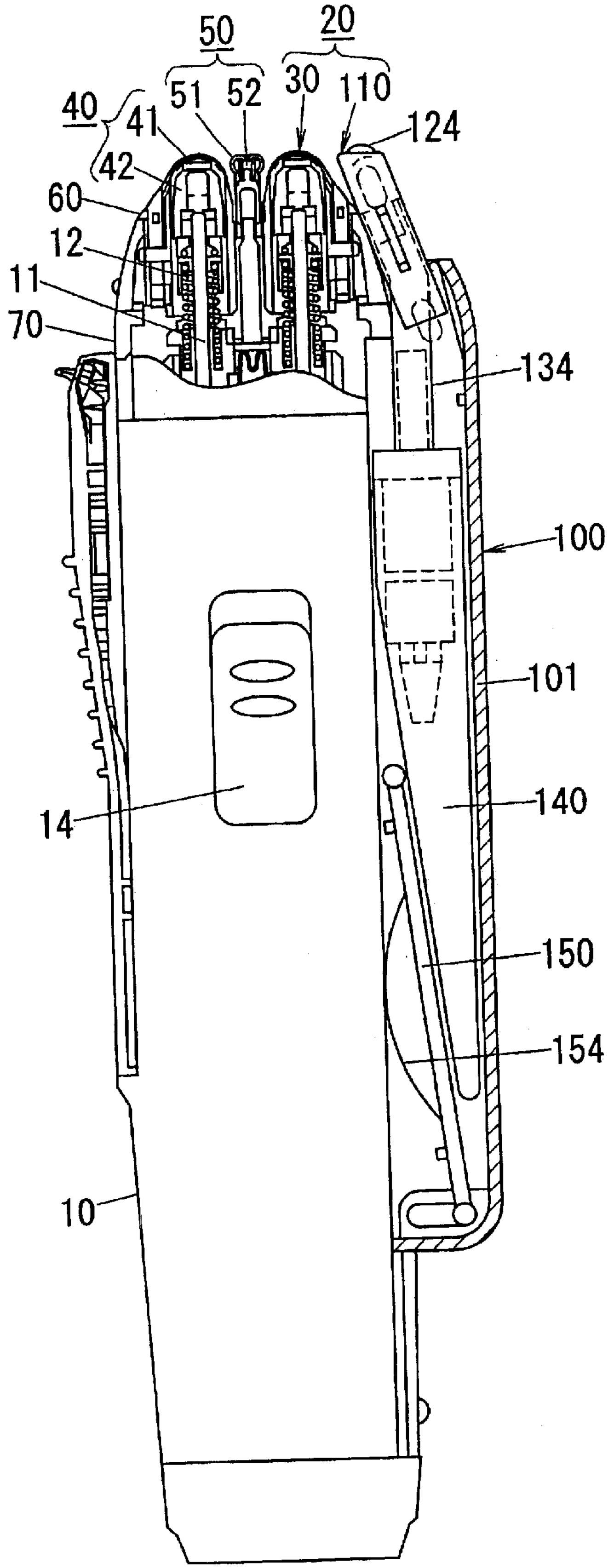
FIG. 1 is a side view partly in section of a shaver shown with an applicator in its projected position in accordance with a first embodiment of the present invention.

Referring now to FIG. 1, there is shown a dry shaver as one typical version of the personal hair removing device in accordance with the first embodiment of the present invention. The shaver includes a housing 10 to be grasped by a hand of a user, and a treatment head 20 which projects on top of the housing 10 and includes a shaving unit, i.e., or hair removing unit 30 as well as an applicator 110 for feeding a lotion on a user's skin. The hair removing unit 30 is composed of three hair cutting sections, namely, a pair of short-hair cutters 40 and a long-hair cutter 50 interposed between the short-hair cutters 40. The short-hair cutter 40 has a U-shaped outer shearing foil 41 and an inner cutter 42 which is driven to oscillate in shearing engagement with the foil, while the long-hair cutter 50 is composed of a slender outer cutter 51 and an inner cutter 52 driven to oscillate in shearing engagement with the outer cutter. The outer shearing foil 41 and the long hair cutter 50 are floatingly supported to a top frame 60 detachably supported to a base frame 70 which is held on top of the housing 10. The housing 10 incorporates an electric motor (not shown) which is connected to oscillate driving elements 11 to which the inner cutters 42 and 52 are coupled. The inner cutters 42 are urged upwardly by bias springs 12 so that the short-hair cutters 40 can be depressed when pressed against a user's skin. The long-hair cutter 30 is biased by a like spring provided in the top frame 60 to be capable of being depressed relative to the top frame or the housing. A switch handle 14 is provided on one side of the housing 10 to activate the motor and therefore oscillate the inner cutters for shaving.

Figure 2:
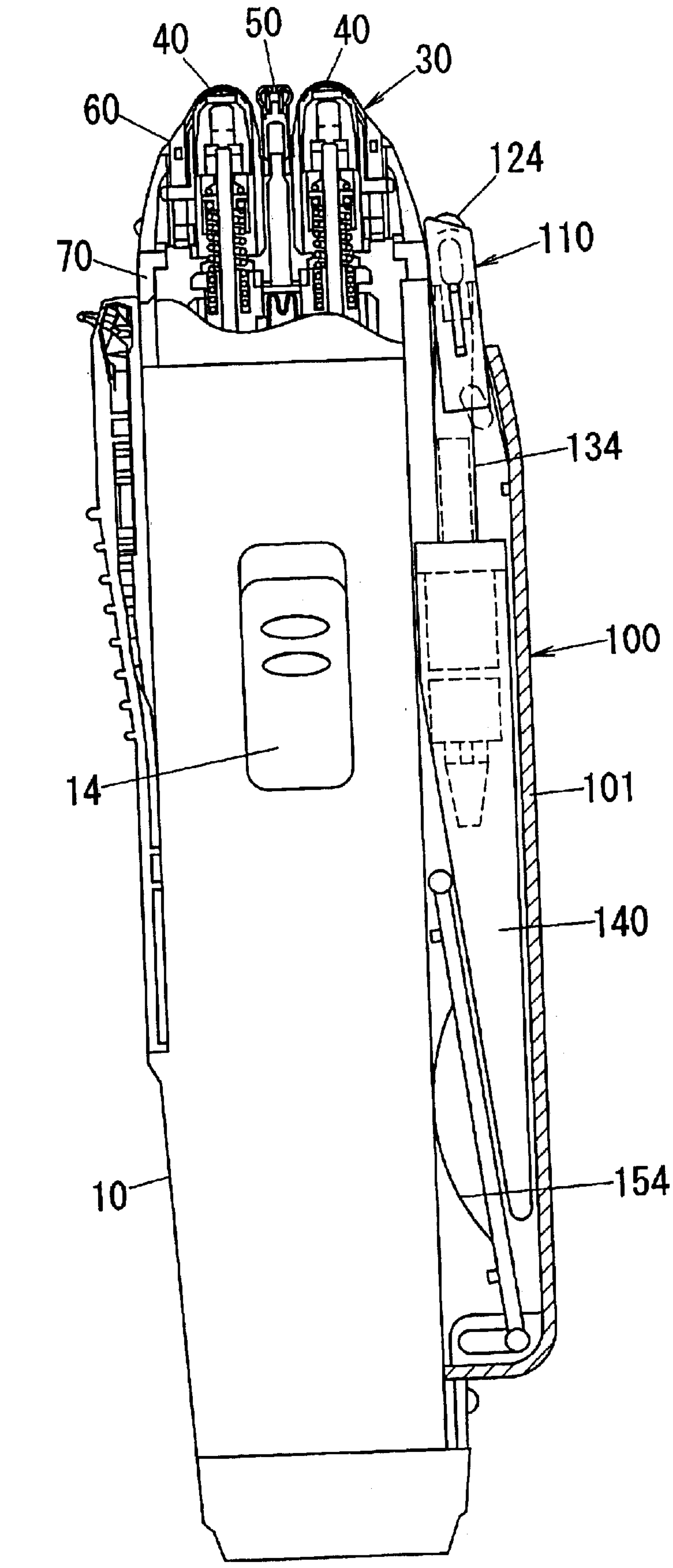
FIG. 2 is a side view partly in section of the shaver with the applicator in its retraced position.

Provided on a front face of the housing 10 is a lotion feeding module 100 which includes the applicator 110 disposed adjacent to the short-hair cutter 40 for dispensing the lotion on the user's skin being shaved or to be shaved. The applicator 110 is held movable between a projected position where it is close to the shaving unit 30, as shown in FIG. 1, and a retracted position where it is away from the shaving unit 30, as shown in FIG. 2. The applicator 110 is floatingly supported to the module 100 and therefore the housing 10 through the module, so that it is capable of being depressed against a spring bias from the projected position to the retracted position, thereby being permitted to follow the contour of the skin easily while the shaver is manipulated to move across the skin.

Figure 3:
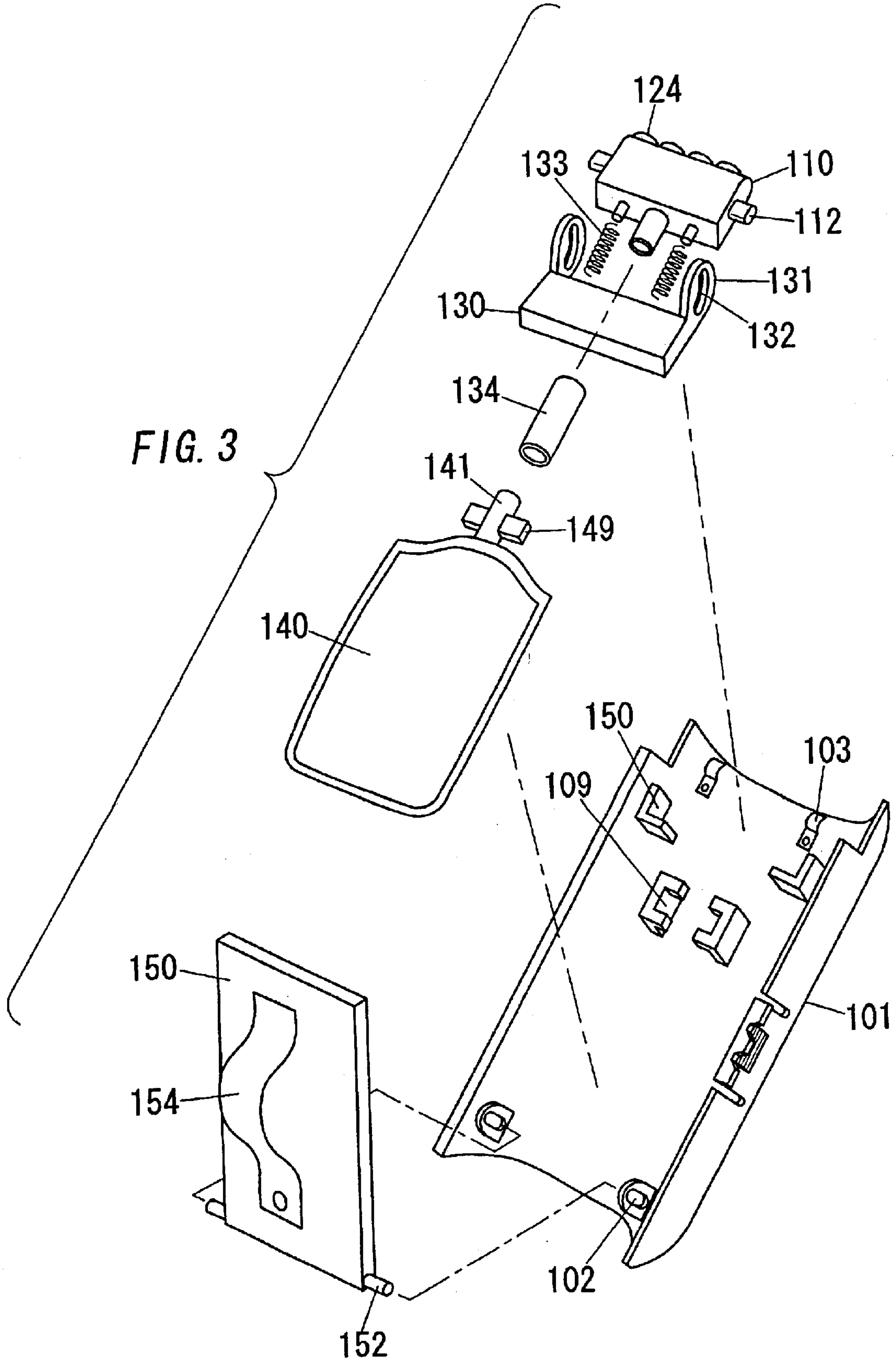
FIG. 3 is an exploded perspective view of a lotion feeding module utilized in the above shaver.

As shown in FIG. 3, the module 100 includes a shell 101 provided with a holder 130 carrying the applicator 110, a flexible tank 140 storing the lotion, and a pressurizer 150 in the form of a plate which is pressed against the tank 140. The tank 140 has a mouth 141 with a hook 149 and is fitted on back of the shell 101 with the hook 149 engaged to a recess 109 of the shell 101. Thus, the module is prepared in a single structure and is detachable to the housing 10. The pressurizer 150 is provided at its lower end with pivot pins 152 which are fitted in corresponding holes 102 in the lower end of the shell 101 so that the pressurizer is caused to be pressed against the tank 140 by an action of a leaf spring 154 formed on back of the pressurizer 150 in close contact with the housing 10, as shown in FIGS. 1 and 2. When the module 100 is detached from the housing 10, the pressurizer can be detached from the shell in order to take out the tank 140 for refilling the lotion or replacement of the tank 140 itself.

Figure 4:
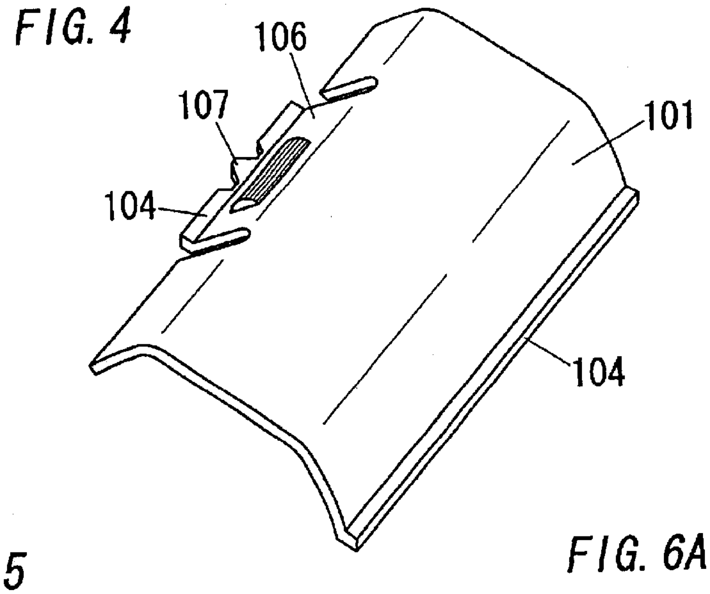
FIG. 4 is a perspective view of the above module.
Figure 5:
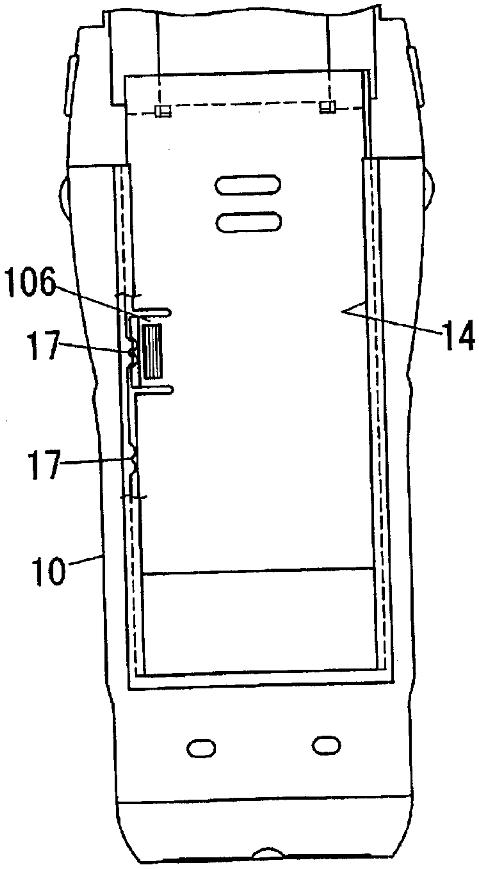
FIG. 5 is a front view of the shaver shown with the module attached.
Figure 6A:
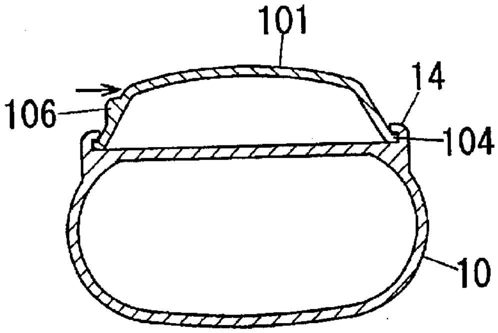
FIGS. 6A and 6B are sectional views showing how to open the above module.
Figure 6B:
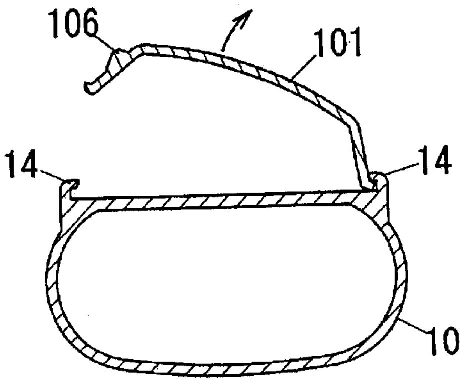

Referring to FIGS. 4 to 6, the shell 101 is made of a rather soft plastic material and has its lateral edges 104 fitted inside of rails 14 formed on the front face of the housing so as to be vertically slidable relative to the housing between the projected position and the retracted position. Formed at one lateral edge of the shell 101 is a resiliently deformable button 106 with the edge 104 and a latch 107 which is locked selectively into one of detents 17 in the corresponding rail 14 on the housing 10 so that the module 100 can be latched in either of the projected and retracted position. As shown in FIGS. 6A and 6B, when the button 106 is pushed inwardly, it is resiliently deformed to release the latch 107 from the detent 17 and at the same time release the edge 104 from the rail 14, thereby being permitted to open and to be removed from the housing 10.

Turning back to FIG. 3, the holder 130 is configured to movably support the applicator 110 relative to the holder in such a manner that the applicator 110 is oriented to have its top lotion feeding end in closely adjacent relation to the short-hair cutter 40 when the applicator is held in its upper most position, as shown in FIG. 1. As the applicator 110 is depressed, it becomes closer to straight in order to avoid interfering with the short-hair cutter 40 of which overall section is wider towards its bottom than at its top along an upright axis of the housing 10 or the shaving unit 30. In addition, when the applicator 110 is lowered to the retracted position in consequence of the module 110 is lowered as shown in FIG. 2, the applicator 110 is kept straight without interfering with the base frame 70. For this purpose, the holder 130 includes a pair of yokes 131 with an elongated slits 132 which are inclined with respect to the upright axis and receive respective horizontal pins 112 of the applicator 110 loosely such that the applicator 110 has its vertical axis inclined at a certain angle with respect to the upright axis to place the top end of the applicator 110 closely to the adjacent shaving unit 30 or the short-hair cutter 40 when the applicator 110 is the uppermost position. In order to keep the applicator 110 inclined towards the shaving unit, the shell 101 includes leaf springs 103 which are held in pressed contact with the applicator 110. Coils springs 133 are interposed between the holder 130 and the applicator 110 to bias the applicator upwardly, i.e., floatingly support the applicator. The holder 130 is retained to the shell 101 by means of shoulders 105 formed inside of the shell. When the applicator 110 is depressed against the bias of the springs 133, the pins 112 are guided along the length of the slits 132 to change the posture of the applicator, i.e., make the vertical axis of the applicator closer in parallel with the upright axis of the housing 10, as indicated by dotted line in FIG. 8B.

Figure 7B:
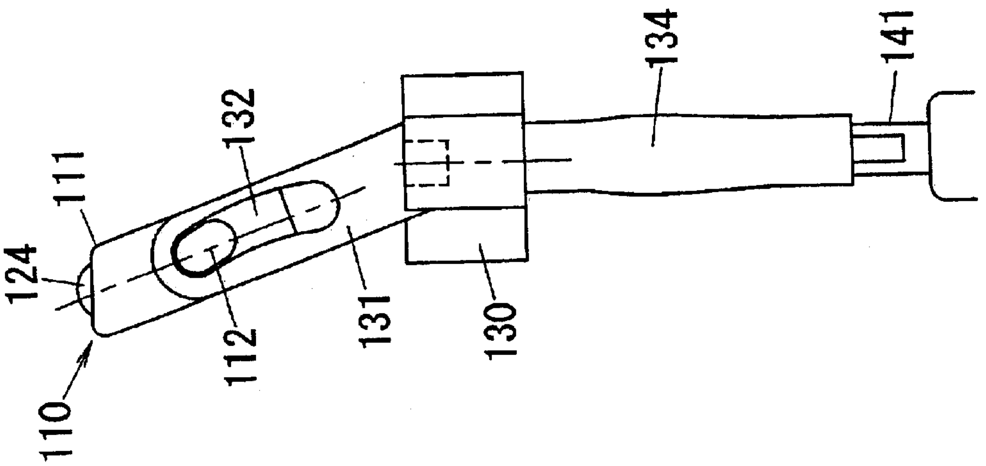
FIGS. 7A and 7B are front sectional view and a side view of the applicator, respectively in its non-depressed condition.
Figure 7A:
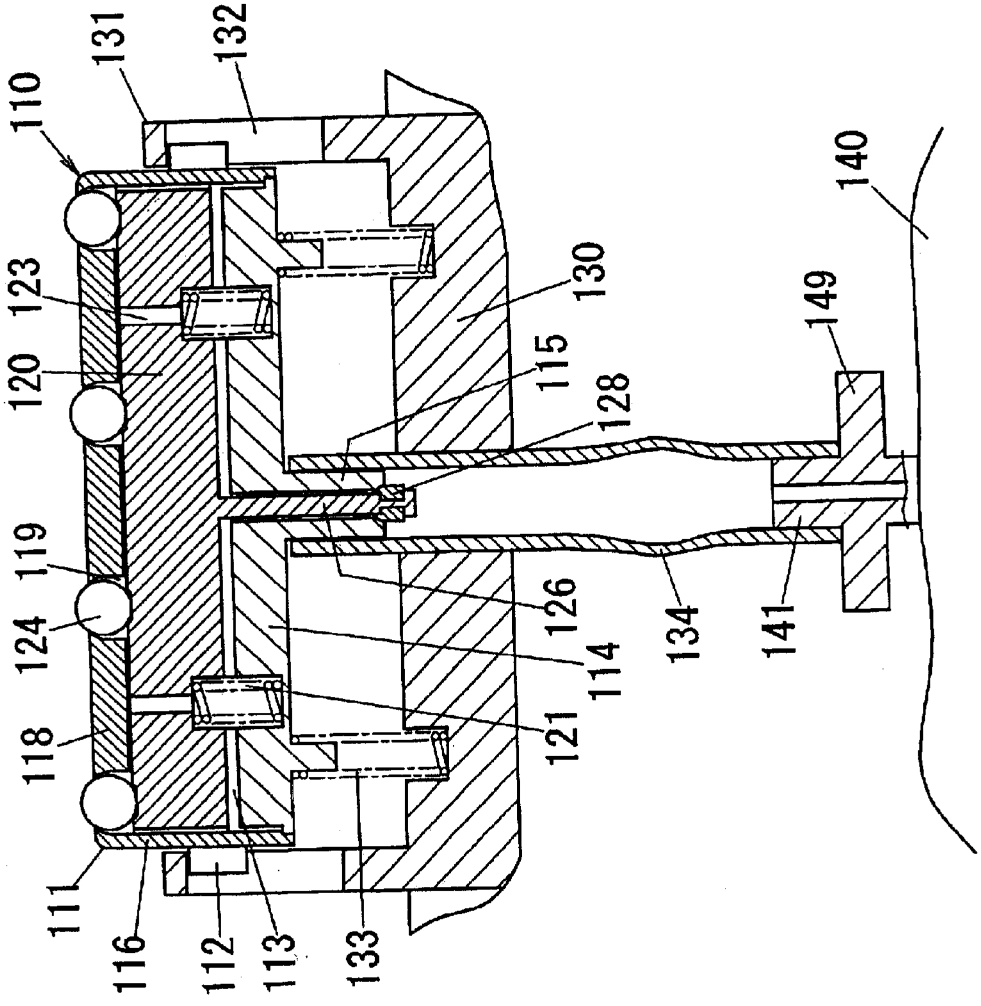
Figure 8B:
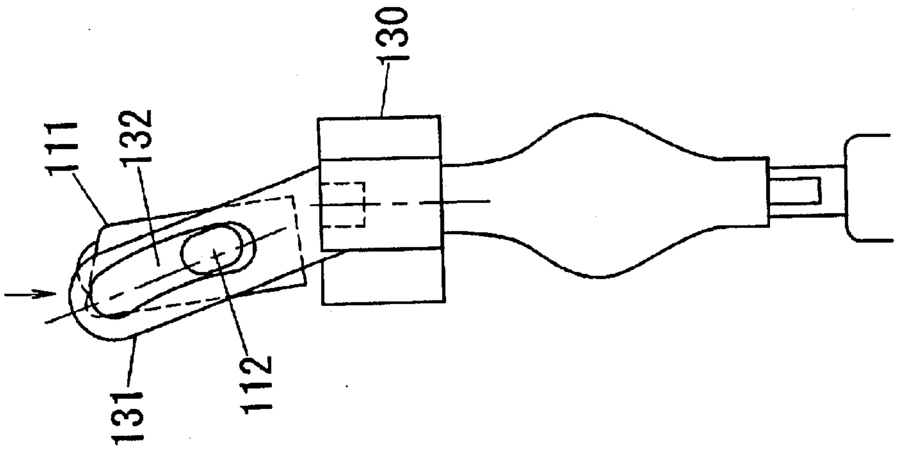
FIGS. 8A and 8B are front sectional view and a side view of the applicator, respectively in its depressed condition.
Figure 8A:
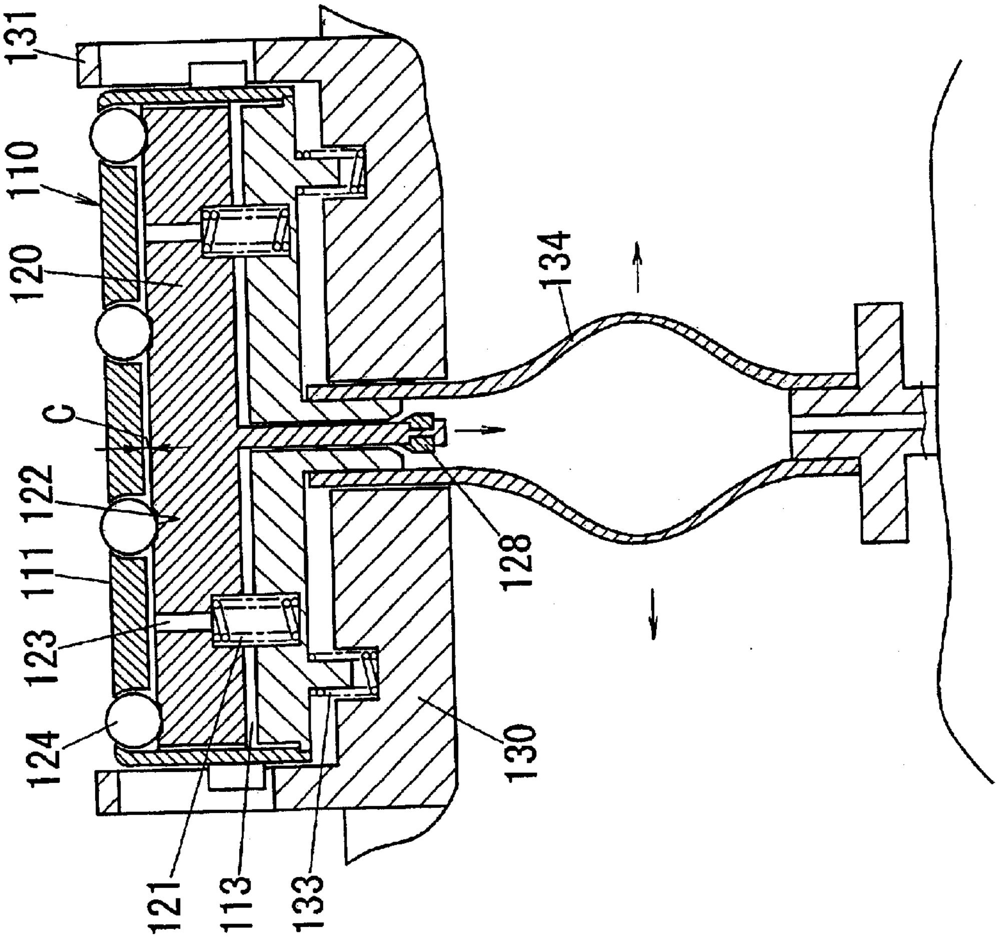
Figure 9B:
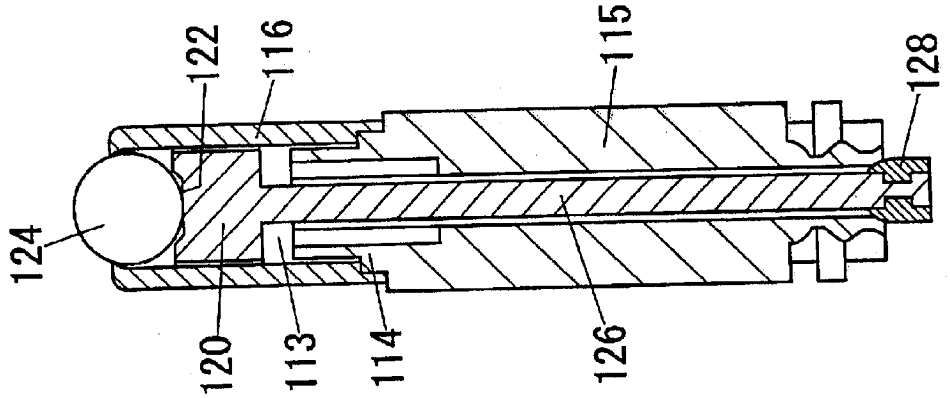
FIGS. 9A and 9BB are front sectional view and a side sectional view of a modified applicator, respectively in its non-depressed condition.
Figure 9A:
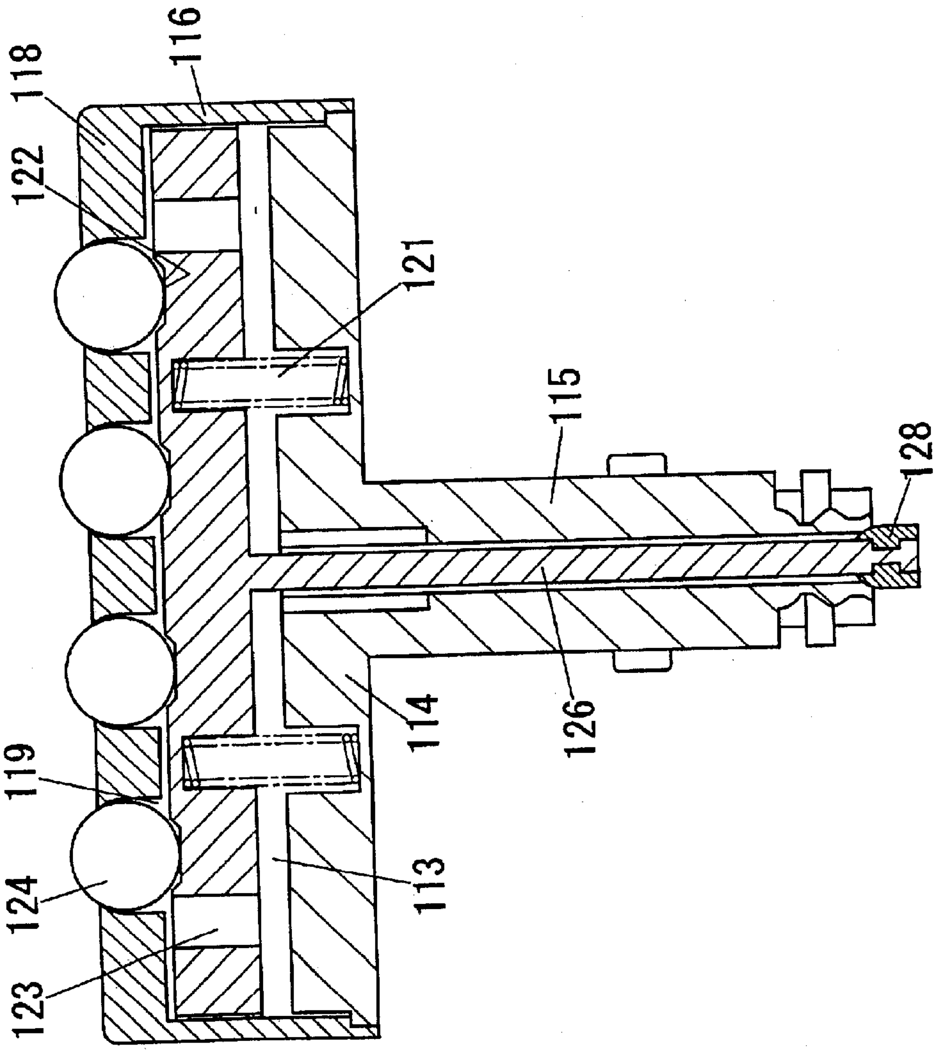
Figure 10B:
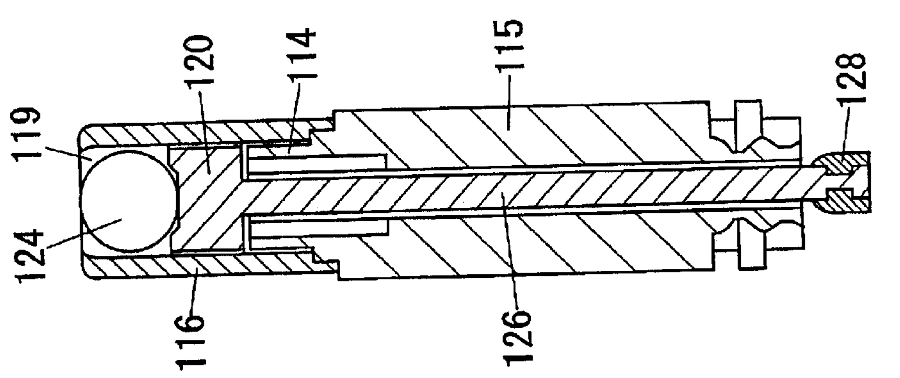
FIGS. 10A and 10B are front sectional view and a side sectional view of the modified applicator, respectively in its depressed condition.
Figure 10A:
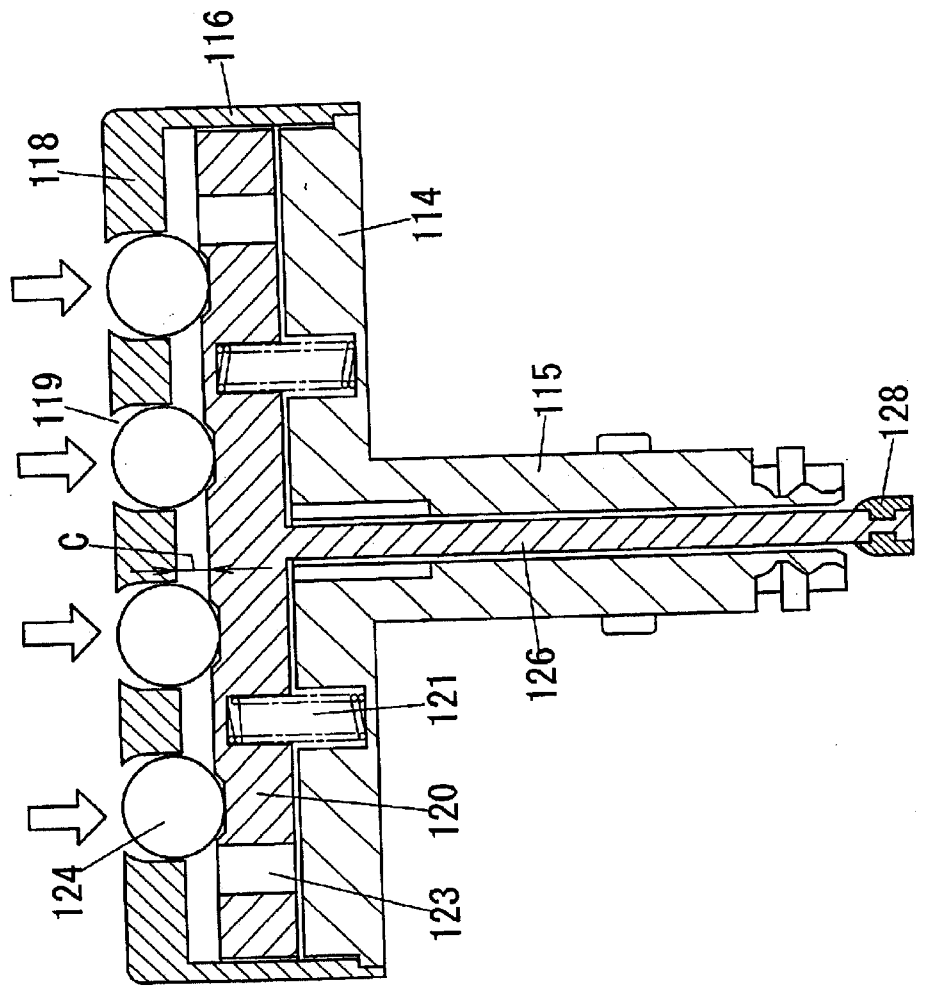

As best shown in FIGS. 7 and 8, the applicator 110 includes a header 111 having a chamber 113 for temporarily storing the lotion supplied from the tank 140. In detail, the header 111 is in the form of a hollow casing with a bottom wall 114, side walls 116, and a top wall 118, and includes a floating bed 120 which is vertically movable within the chamber and is floatingly supported to the bottom wall 114 by means of coil springs 121. A plurality of rotating elements or balls 124 are loosely fitted respectively within apertures 119 formed in the top wall 118 so as to come into rolling contact with the skin when the applicator 110 is held against the skin. The apertures 119 communicate with the chamber 113 directly or through riser channels 123 in the floating bed 120 such that the lotion is dispensed through a clearance between the aperture 119 and the ball 124 for feeding the lotion over the skin while the balls rotate in contact with the skin. The balls 124 are supported on the floating bed 120 so as to be capable of being depressed together therewith against the bias of the springs 121, as shown in FIG. 8A, as a consequence of the applicator 110 being pressed against the skin. The balls 124 are seated respective in shallow cavities 122 in the top surface of the floating bed 120, and are kept retained in the apertures 119 by narrowed opening edges thereof when urged upwardly by the action of the springs 121. The chamber 113 communicates with the tank 140 through a sleeve 115 integrally projecting from the bottom wall 114 and a flexible tube 134 of which opposite ends are sealed respectively to the sleeve 115 and the mouth 141 of the tank 140. Projecting downward from the floating bed 120 is a stem 126 which extends loosely through the sleeve 115 and is provided at its bottom with a stop valve 128 in sealing contact with a bottom open end of the sleeve 115, whereby a lotion feed path from the tank 140 to the applicator is normally closed by the stop valve 128, as shown in FIGS. 7A The stop valve 128 is opened only when the floating bed 120 is depressed together with the balls 124, as shown in FIG. 8A. Thus, the lotion under being pressurized in the tank 140 can be supplied to the applicator 110 in response to the balls 124 being pressed against the user's skin. In this sense, the stop valve 128 is cooperative with the pressurizer 150 to define a lotion supply mechanism for supplying the lotion from the tank 140 to the applicator 110, and the balls 124 define an actuator that activate the lotion supply mechanism to supply the lotion from the tank 140 to the applicator 110 for applying the lotion over the skin. It should be noted here that since the applicator 110 is held in closely adjacent relation to the shaving unit 30, the actuator in the form of the balls 124 can be mobilized or depressed when the shaving unit 30 comes into an operative condition for hair shaving, enabling to apply the lotion over the skin easily in association with the shaving, yet requiring no extra switching operation other than pressing the applicator against the user's skin. FIGS. 9 and 10 shows a modification of the header 111 which is identical to the header of FIGS. 7 and 8 except that the riser channels 123 are offset from the springs 121 in order to reduce the height of the header 111. Like parts are designated by like reference numerals. FIGS. 9A and 9B show a non-depressed condition where the balls 124 and the floating bed 120 are not in depressed with the stop valve 128 being kept closed, while FIGS. 10A and 10B shows an operative condition where the balls 124 are depressed together with the floating bed 120 with the stop valve 128 being held opened.

Figure 11:
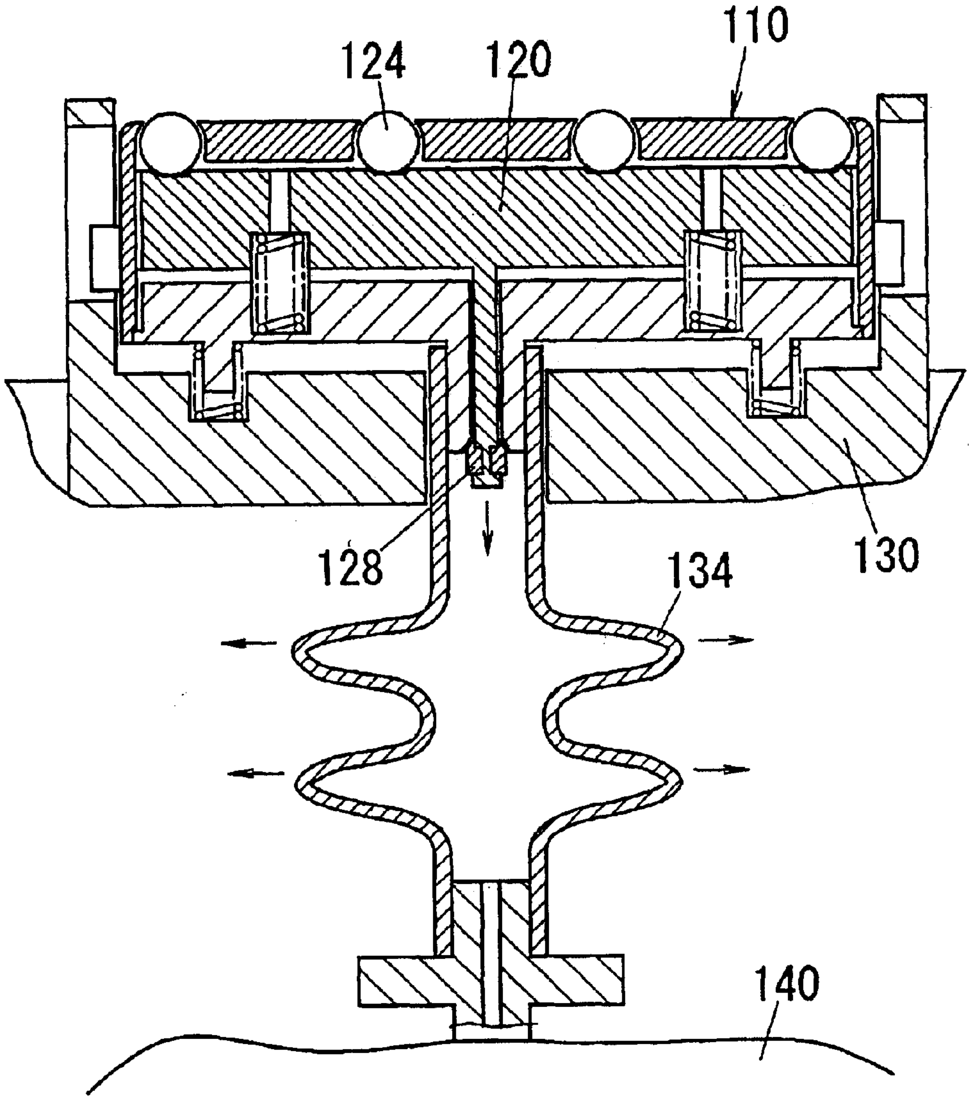
FIG. 11 is a front sectional view of the applicator in accordance with a modification of the above embodiment.

Due to the flexible nature, the tube 134 absorbs the resulting displacement of the applicator 110 relative to the tank 140 as being radially deformed as indicated by arrowed lines in FIG. 8A. It is noted in this connection, as the balls 124 is depressed or lowered together with the floating bed 120 as shown in FIGS. 8A, 10A, and 10B, the balls 124 are caused to rotate freely for smooth rolling contact with the skin, and therefore efficient lotion feeding over the skin. In this condition, the pressurized lotion is supplied through the riser channels 123 into an enlarged clearance C between the lowered floating bed 120 and the top wall 118 from which the lotion is dispensed through the action of the balls 124. As shown in FIG. 11, the applicator 110 may be connected to the tank 140 through a tube 134 in the form of a bellows.

Figure 12B:
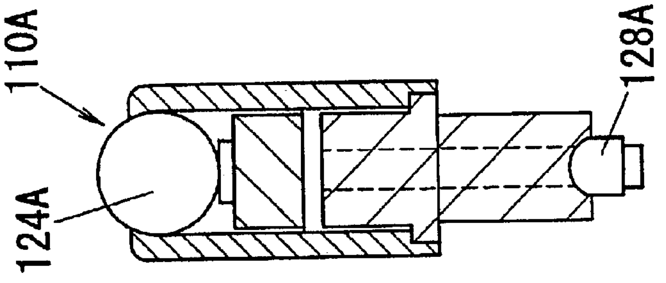
FIGS. 12A and 12B are front sectional view and a side sectional view, respectively of an applicator in accordance with another modification of the above embodiment.
Figure 12A:
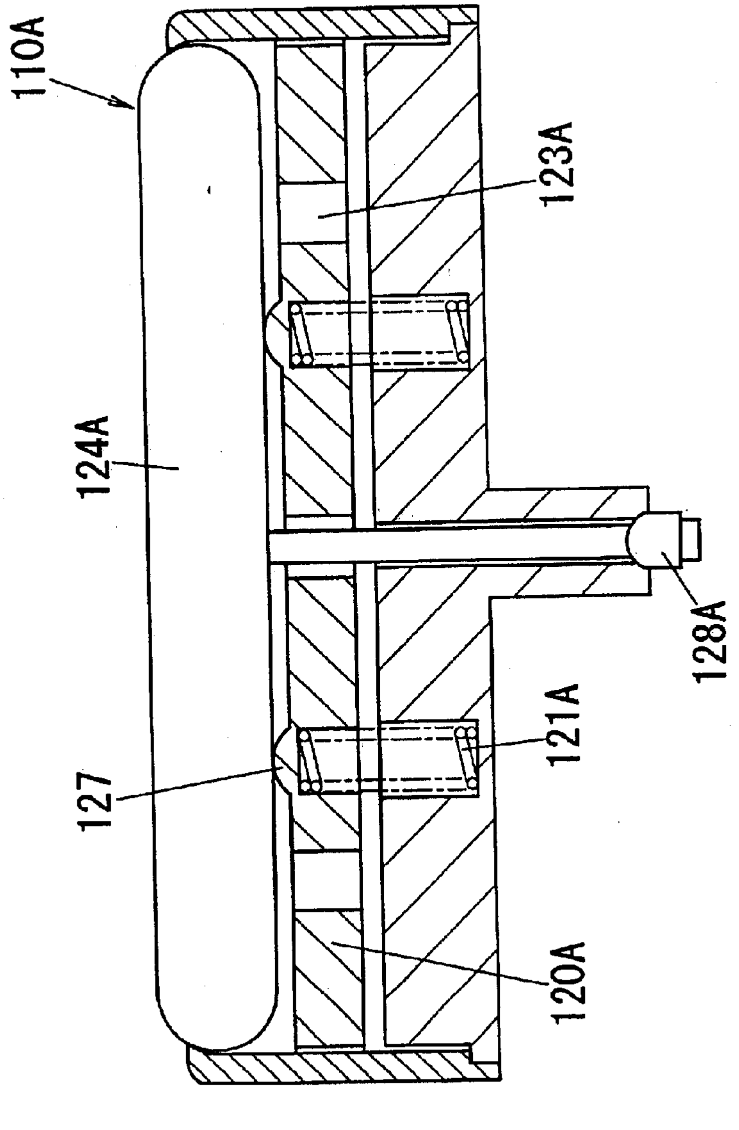

As shown in FIGS. 12A and 12B, the applicator 110A may utilize a roller 124A instead of the balls for applying the lotion. In this modification, the roller 124A is supported on the floating bed 120A by means of rounded projections 127 so as to be capable of rotating about a horizontal axis for rolling contact with the user's skin. Like parts are designated by like numerals with a suffix letter of "A". The balls 124 and the rollers 124A may be made of elastic material for soft and comfortable contact with the user's skin.

Figure 13B:
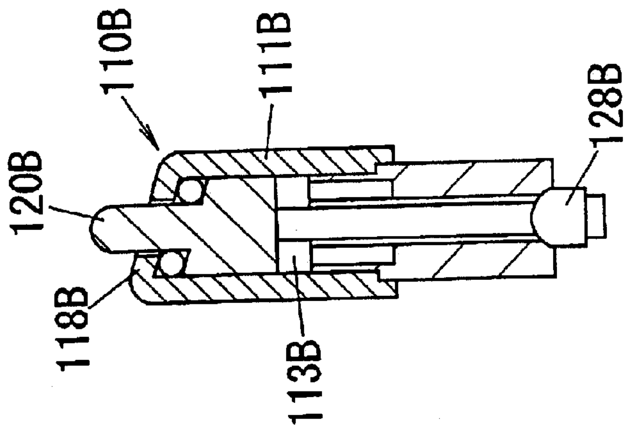
FIGS. 13A and 13B are front sectional view and a side sectional view, respectively of an applicator in accordance with a further modification of the above embodiment.
Figure 13A:
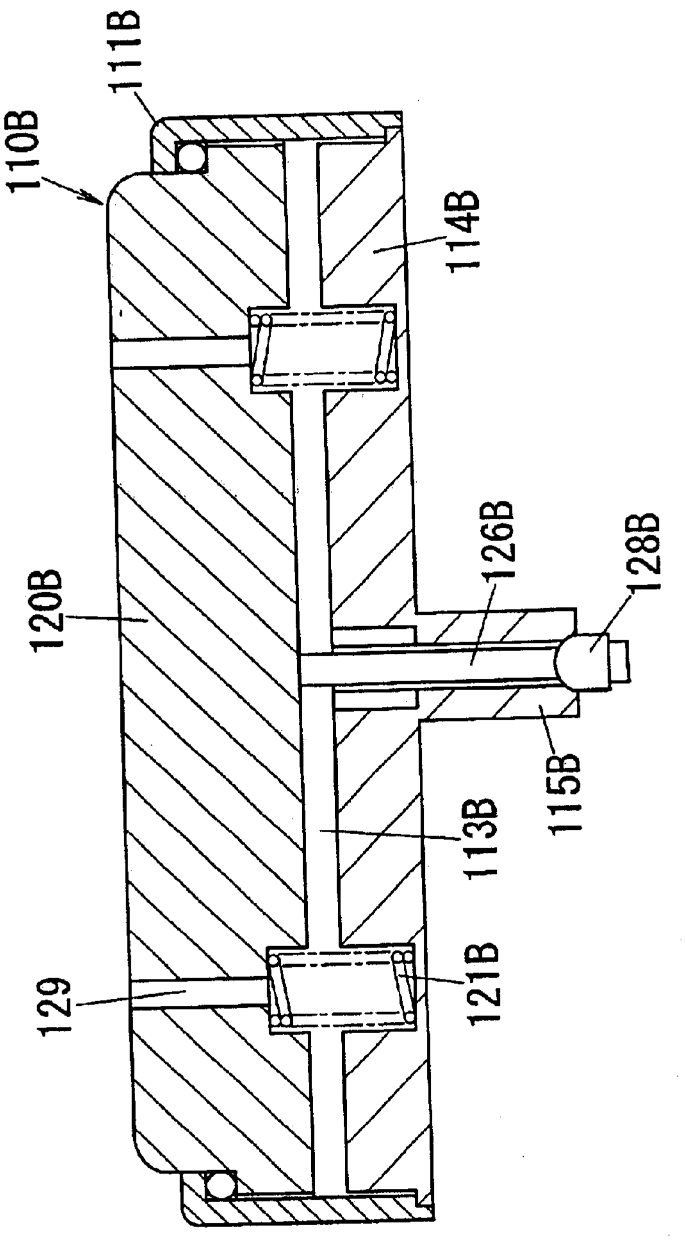

As shown in FIGS. 13A and 13B, the applicator 110B may include a skin guide 120B as one modification of the floating bed 120 depicted in the above embodiment. The skin guide 120B is made of an elastic material and has its top end projecting above the top wall 118B of the header 111B for contact with the user's skin and has its bottom spaced from the bottom wall 114B to define therebetween a like chamber 113B for temporarily storing the lotion supplied from the tank. Apertures 129 are formed in the skin guide 120B for dispensing the lotion from the chamber 113B over the user's skin. Also formed on the skin guide 120B is a like stop valve 128B for opening and closing the lotion flow path from the tank to the chamber. The skin guide 120B is biased upwardly by means of coil springs 121B so as to be capable of being depressed. When the skin guide 120B is depressed upon contact with the user's skin, the stop valve 128B is opened to allow the lotion to be supplied to the chamber 113B from the tank, and therefore dispensing the lotion over the user's skin through the apertures 129. In this modification, the skin guide 120B defines the actuator which senses the applicator being depressed and open the valve 128B for supplying the lotion from the tank to the chamber 113B, allowing the lotion to be dispensed. Like parts are designated by like reference numerals with a suffix letter of "B".

Figure 14:
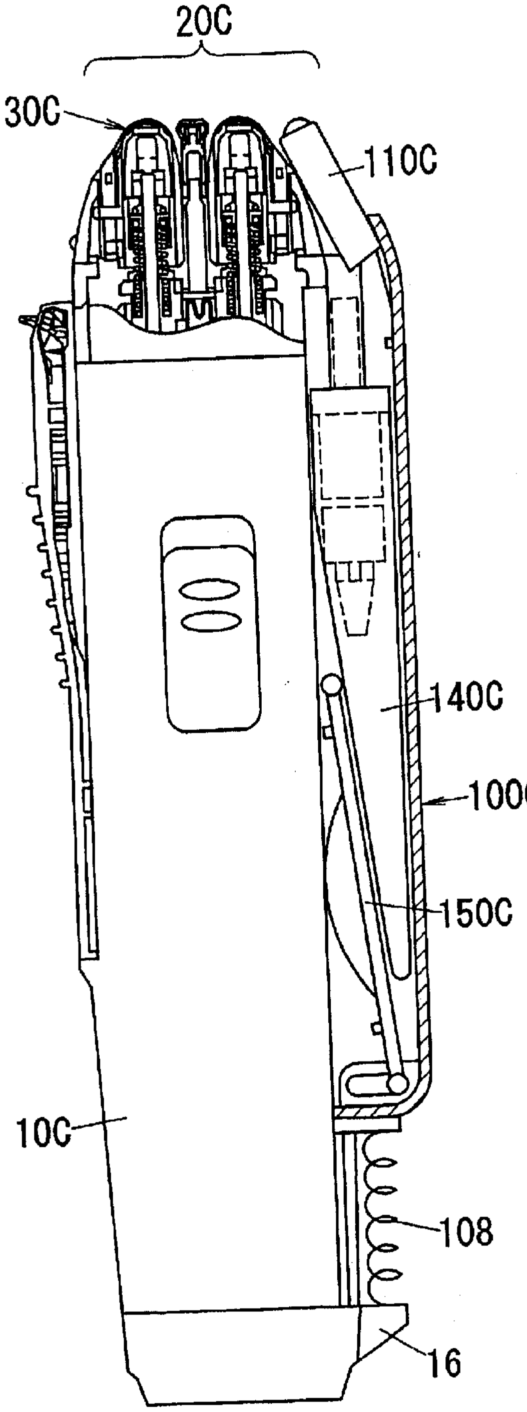
FIGS. 14 and 15 are side views partly in section of a shaver with an applicator shown in its projected position and retracted position, respectively in accordance with a further modification of the above embodiment.
Figure 15:
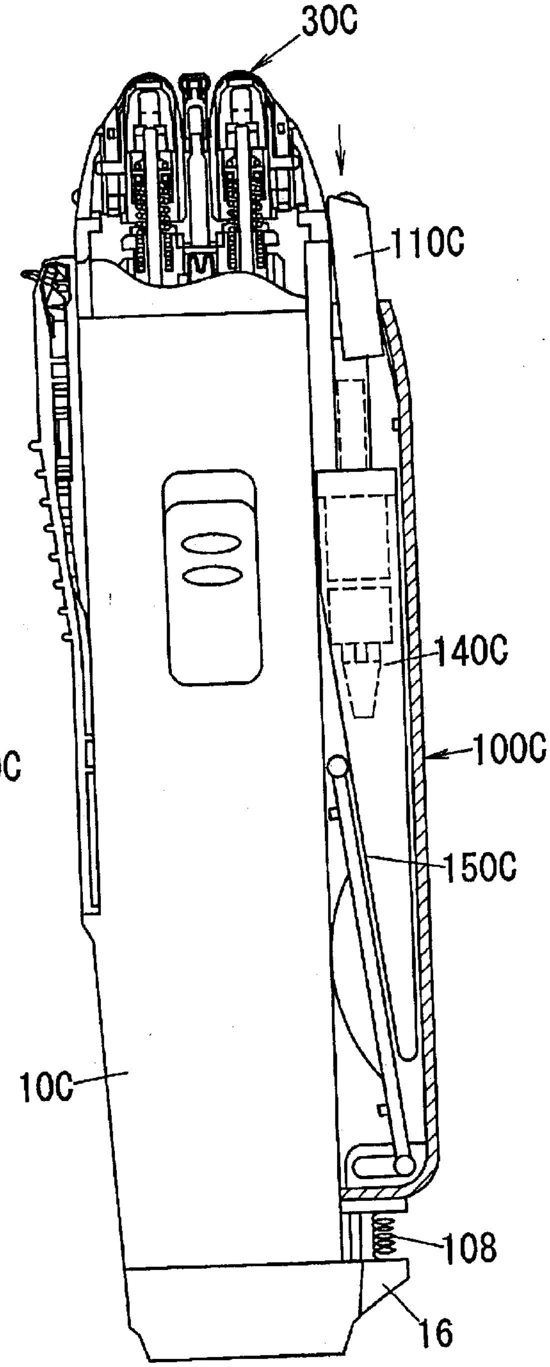
Figure 16:
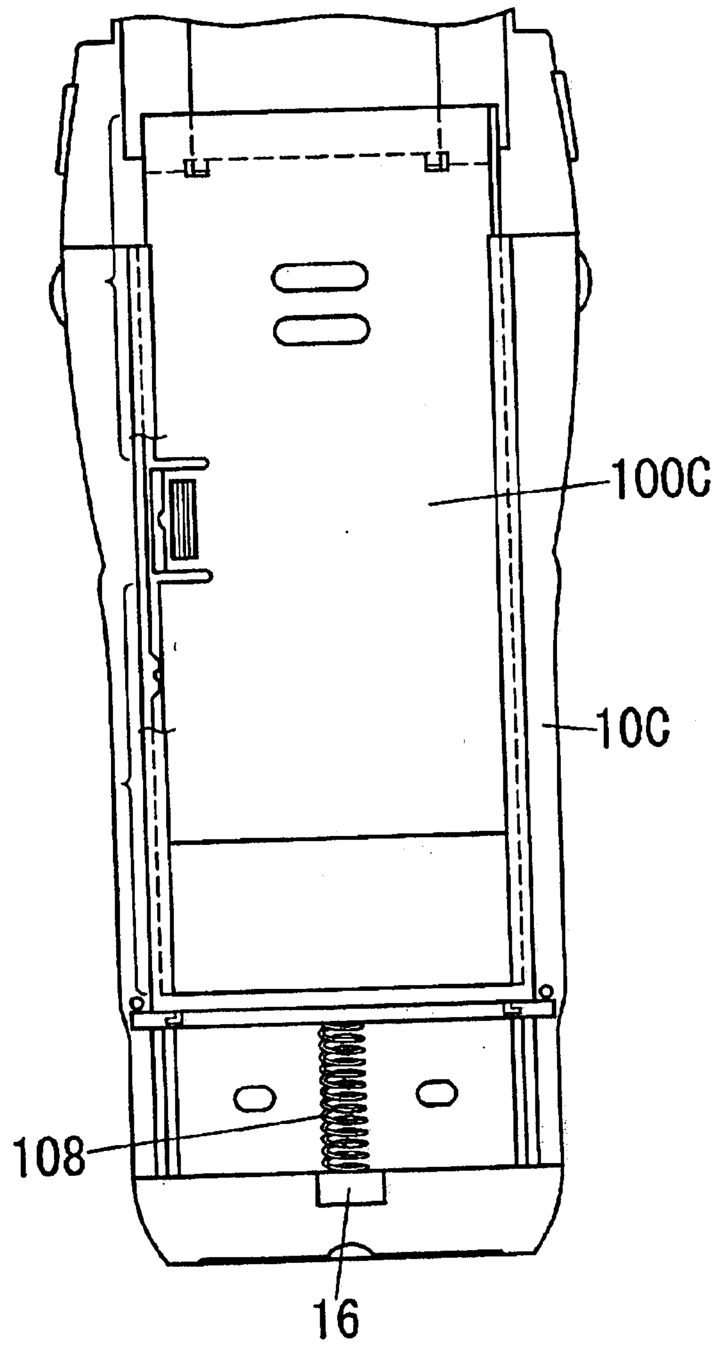
FIG. 16 is a front view of the shaver of FIG. 14.

FIGS. 14 to 16 show a modification of the device which is substantially identical to the above embodiment except that the lotion feeding module 100C is itself floatingly supported to the housing 10C by means of a coil spring 108 interposed between the lower end of the module 100C and a bottom flange 16 of the housing 10C. Thus, the module can be vertically movable between the projected position of FIG. 14 and the retracted position of FIG. 15, and is latched in either of these positions. Like parts are designated by like reference numerals with a suffix letter of "C".

Figure 17:
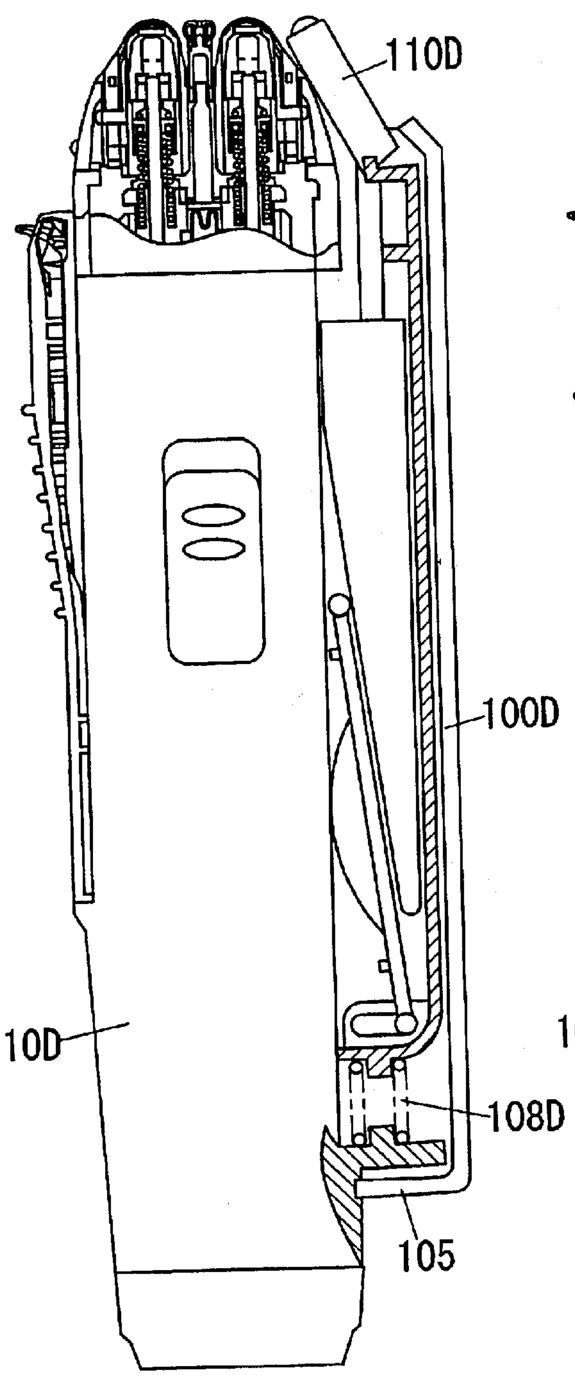
FIGS. 17 and 18 are side views partly in section of a shaver with an applicator shown in its projected position and retracted position, respectively in accordance with a further modification of the above embodiment.
Figure 18:
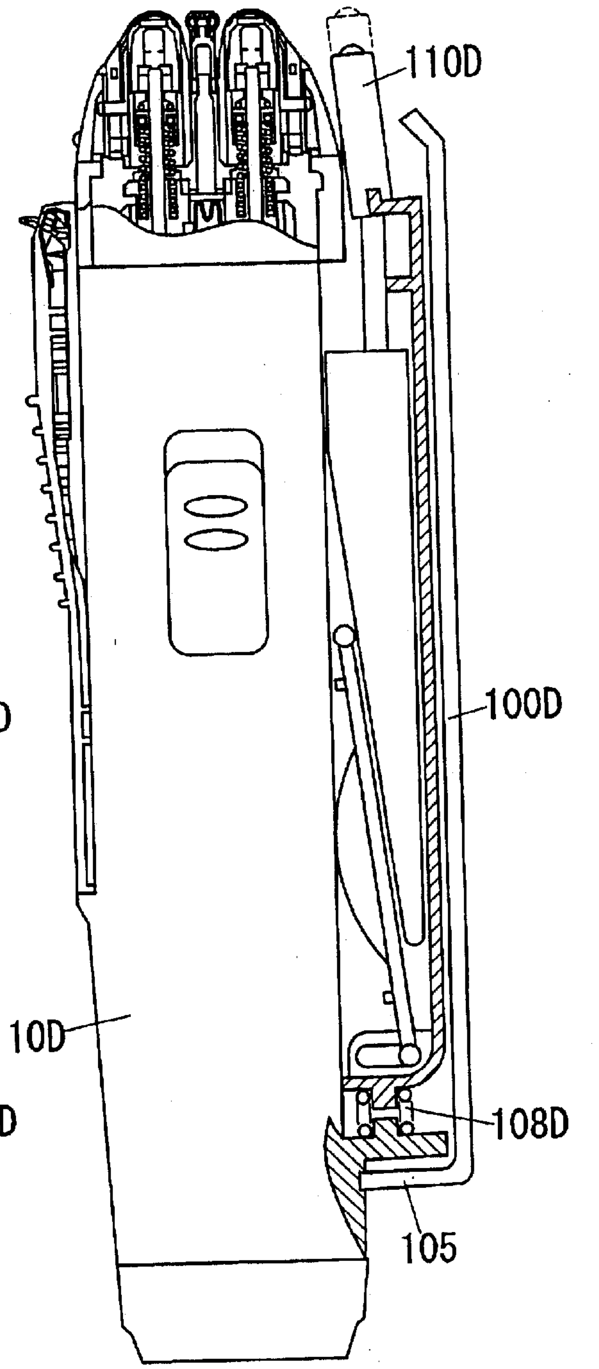

FIGS. 17 and 18 show another modification of the device which is similar to the above modification but the shell 101D of the lotion feeding module 100D has a mask 105 concealing the spring 108D which is provided for floatingly supporting the module 100D. Like parts are designated by like reference numerals with a suffix letter of "D".

Figure 19:
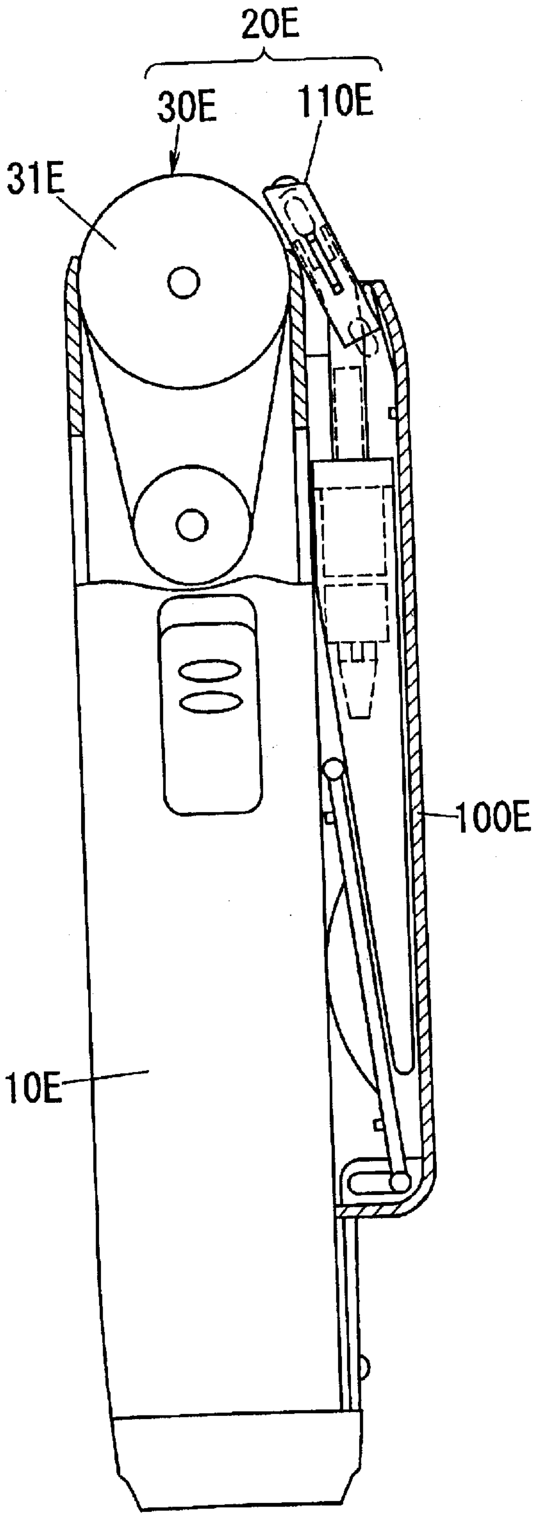
FIGS. 19 and 20 are side views partly in section of an epilating device with a lotion applicator shown in its projected position and retracted position, respectively in accordance with a further modification of the above embodiment.
Figure 20:
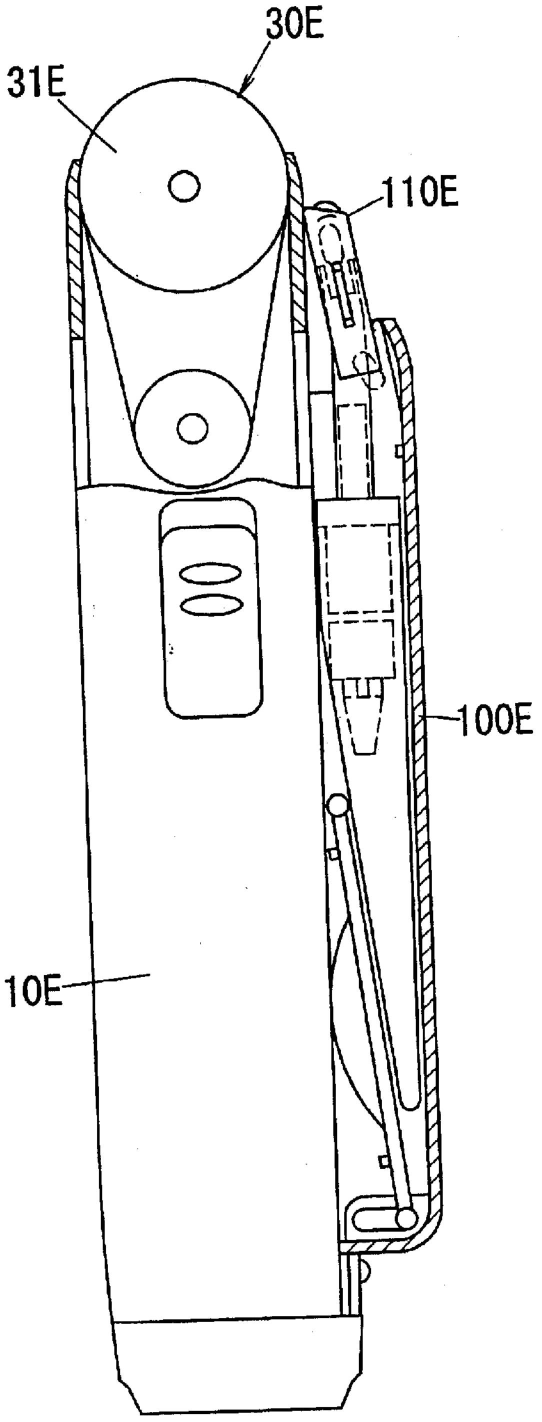

Although the above embodiment illustrates the device provided with the shaving unit 30 as the hair removing or hair depilating unit, the present invention should not be limited thereto and may be equally applied to the device with a hair epilating unit 30E, as shown in FIGS. 19 and 20. The hair epilating unit 30E is mounted on top of the housing 10E and is cooperative with the applicator 110E of the identical structure as the above embodiment to define a treatment head 20E. The epilating unit 30E includes an epilating cylinder 31E which has hair pinching elements and which is driven to oscillate or rotate about a horizontal axis so as to repeat pinching the hairs and plucking the hairs from the user's skin. The applicator 110E is held in close adjacent relation with the epilation unit 30E on the same side of the housing so that the applicator can feed the lotion while the epilating unit is set into an operative condition relative to the user's skin.

Figure 21A:
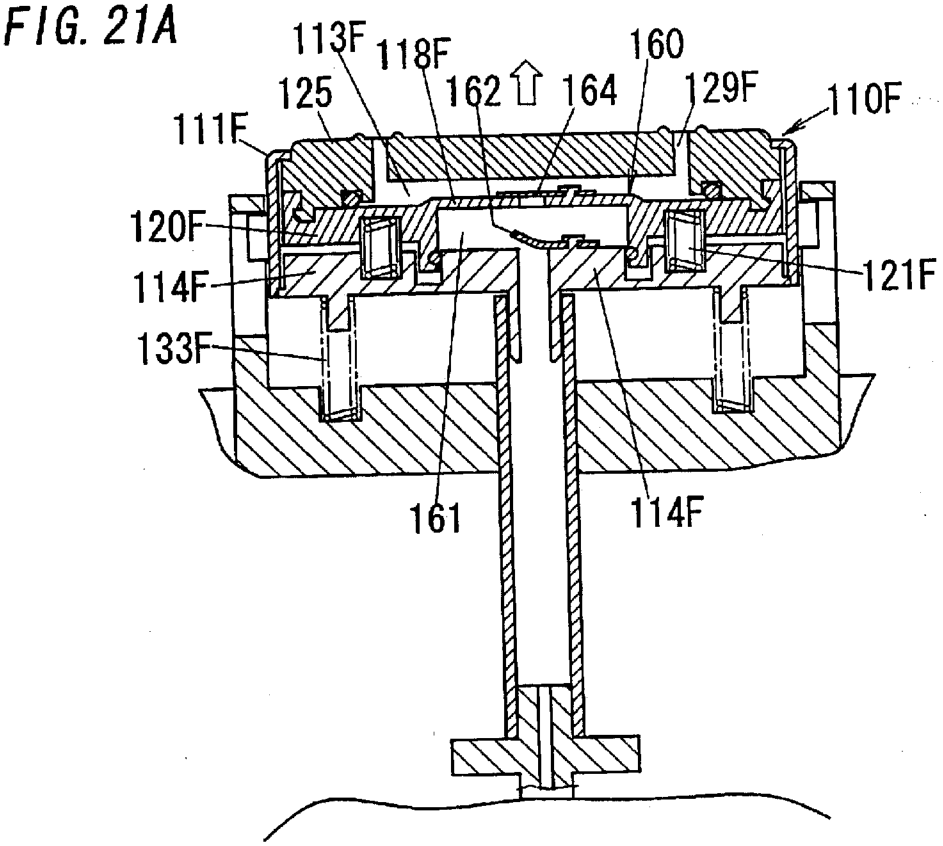
FIGS. 21A and 21B are front sectional views respectively showing a pumping operation of an applicator utilized in the shaver in accordance with a second embodiment of the present invention.
Figure 21B:
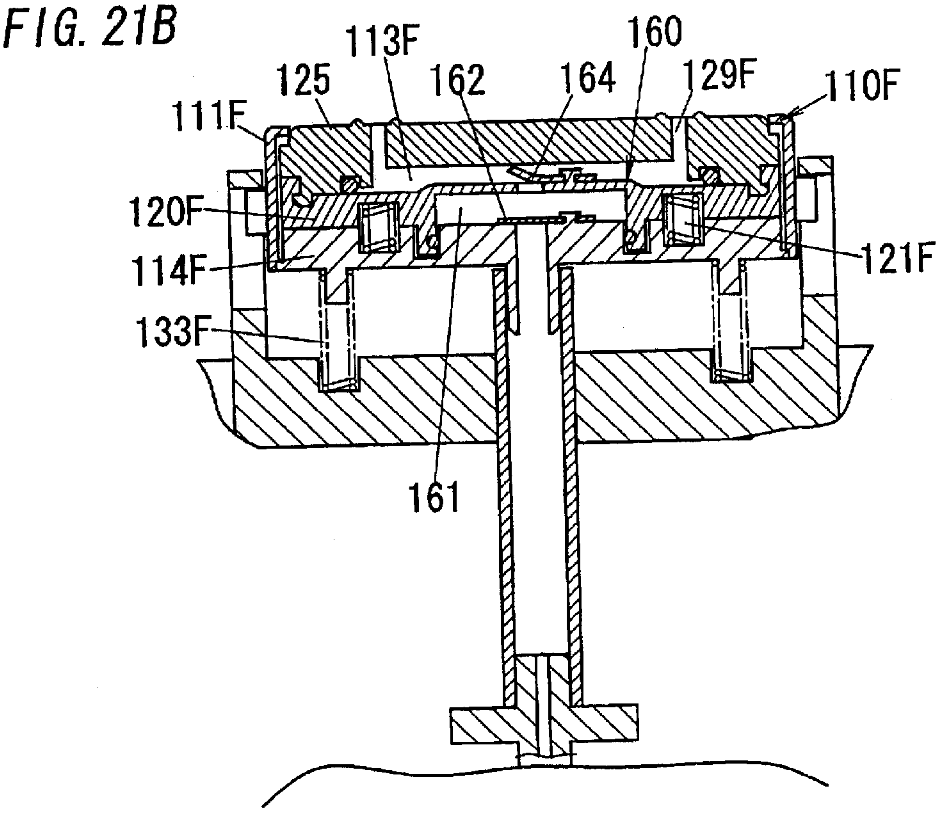

Second Embodiment <FIGS. 21A and 21B>

Referring to FIGS. 21A and 21B, there is shown an applicator of another type which can be utilized in the device. The applicator 110F of the present embodiment is provided with a pump 160 for drawing the lotion from the tank and delivering it to a chamber 113F in the applicator for dispensing the lotion therefrom over the user's skin. For this purpose, the applicator 110F has the header 111F so configured that a floating bed 120F is cooperative with a bottom wall 114F to define the pump 160 having a pump chamber 161 which communicates with the tank through an inlet flap valve 162 and communicates with the chamber 113F through an outlet flap valve 164. In this sense, the pump 160 is defined as one element for constituting the lotion supply mechanism for supplying the lotion from the tank to the applicator. The floating bed 120F is floatingly supported to the bottom wall 114F by means of coil springs 121F to be movable relative to the bottom wall while changing a volume of the pump chamber 161. Fixed to the floating bed 120F is a skin guide 125 which projects on the header for contact with the skin and is provided with apertures 129F in communication with the chamber 113F. Thus, the skin guide 125 of the present embodiment defines the actuator which activates the lotion supply mechanism, i.e., the pump 160 in synchronous with the applicator being pressed against and released from the user'skin.

When the skin guide 125 is depressed as being pressed against the user' skin, the floating bed 120F is lowered together in a direction of reducing the volume of pump chamber 161, as shown in FIG. 21B, so as to generate a positive pressure within the pump chamber, thereby opening the outlet flap valve 164 and delivering the lotion out of the pump chamber for dispensing it through apertures 129F on the user's skin. When, on the other hand, the skin guide 125 returns by the bias of the springs 121F as being released from the user's skin, as shown in FIG. 21A, the floating bed 120F is raised in a direction of increasing the volume of the pump chamber to generate a negative pressure within the pump chamber, thereby closing the outlet flap valve 164 while opening the inlet flap valve 162 for drawing the lotion from the tank into the pump chamber 161. Thus, in response to the skin guide being pressed against and released from the user's skin, the pump is activated to feed the lotion on the user's skin and to draw the lotion from the tank. In this sense, the lotion feed mechanism can be dispensed with the pressurizer for pressurizing the lotion in the tank and also with the stop valve 128 as employed in the above embodiment, yet applying the lotion effectively to the user's skin. Thus configured applicator 110F is floatingly supported to a like holder 130F by means of coil springs 133F as is made in the first embodiment.

Figure 22A:
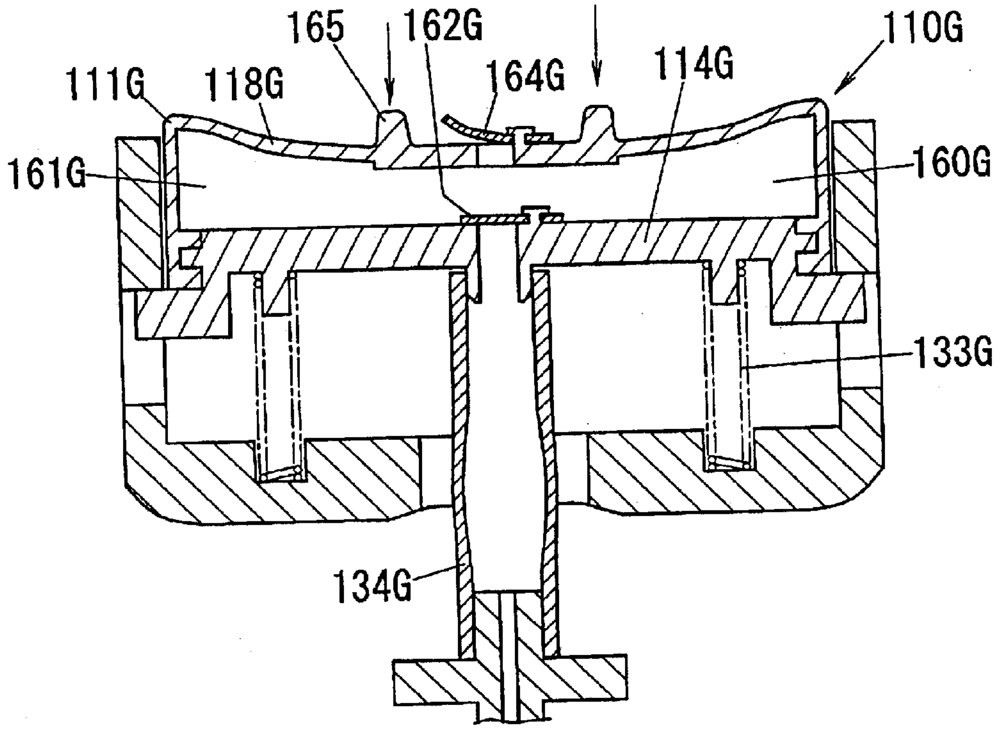
FIGS. 22A and 22B are front sectional views respectively showing a pumping operation of an applicator in accordance with a modification of the second embodiment.
Figure 22B:
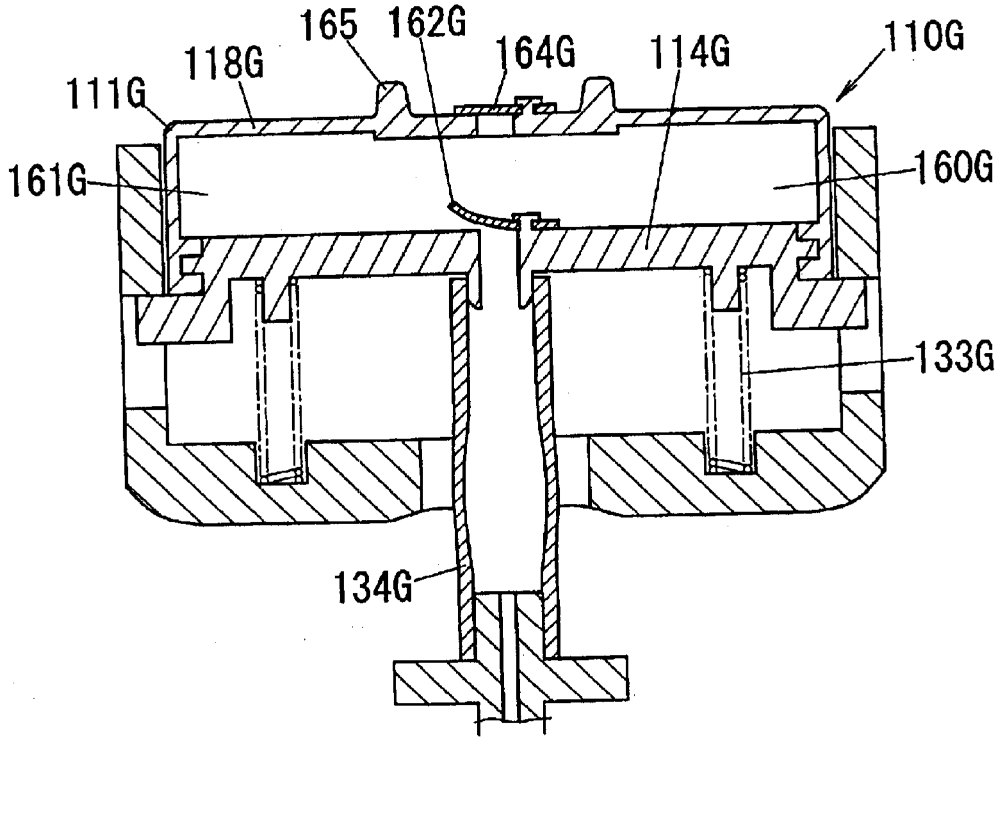

FIGS. 22A and 22B show a modified applicator which is similar to the above embodiment except that the applicator 110G includes a header 111G which defines a skin guide as well as a like pump 160G of drawing the lotion from the tank to the applicator. The header 111G has a resiliently deformable top wall 118G which defines the skin guide and is further cooperative with a bottom wall 114G to define therebetween a pump chamber 161G. The bottom wall 114G is provided with an inlet flap valve 162G, while the skin guide 118G is provided on its external surface with an outlet flap valve 164G and also with an annular projection 165 surrounding the valve 164G for avoiding direct contact of the valve with the user's skin. When the skin guide 118G is depressed, as shown in FIG. 22A, the volume of the pump chamber 161G decreases to thereby open the outlet valve 164G, dispensing the lotion once supplied into the pump chamber 161G. After the skin guide 118G is released from the user's skin, it returns to the position of FIG. 22B, increasing the volume of the pump chamber 161G, thereby opening the inlet valve 162G to draw in the lotion from the tank. In this sense, the skin guide 118G on top of the applicator constitutes the actuator which activates the pump each time the applicator is pressed against and released from the user's skin for effectively applying the lotion in the like manner as in the second embodiment. Like parts are designated by like reference numerals with a suffix letter of "G".

Figure 23A:
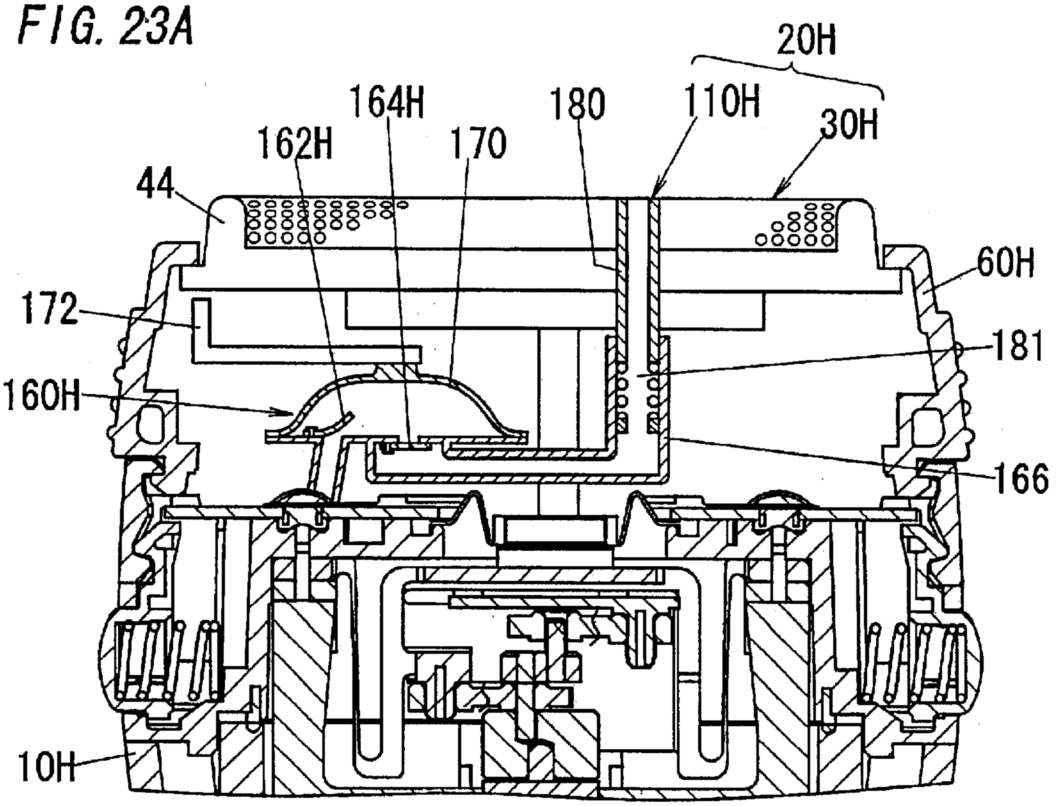
FIGS. 23A and 23B are front sections of a shaver with a lotion applicator in accordance with a third embodiment of the present invention.
Figure 23B:
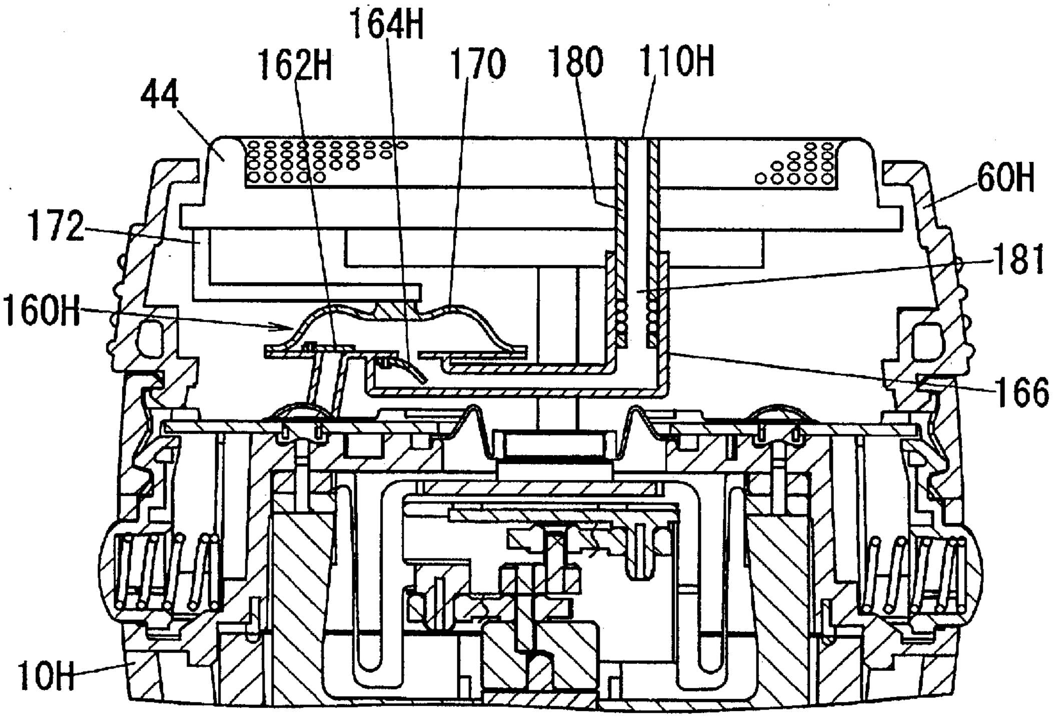
Figure 24:
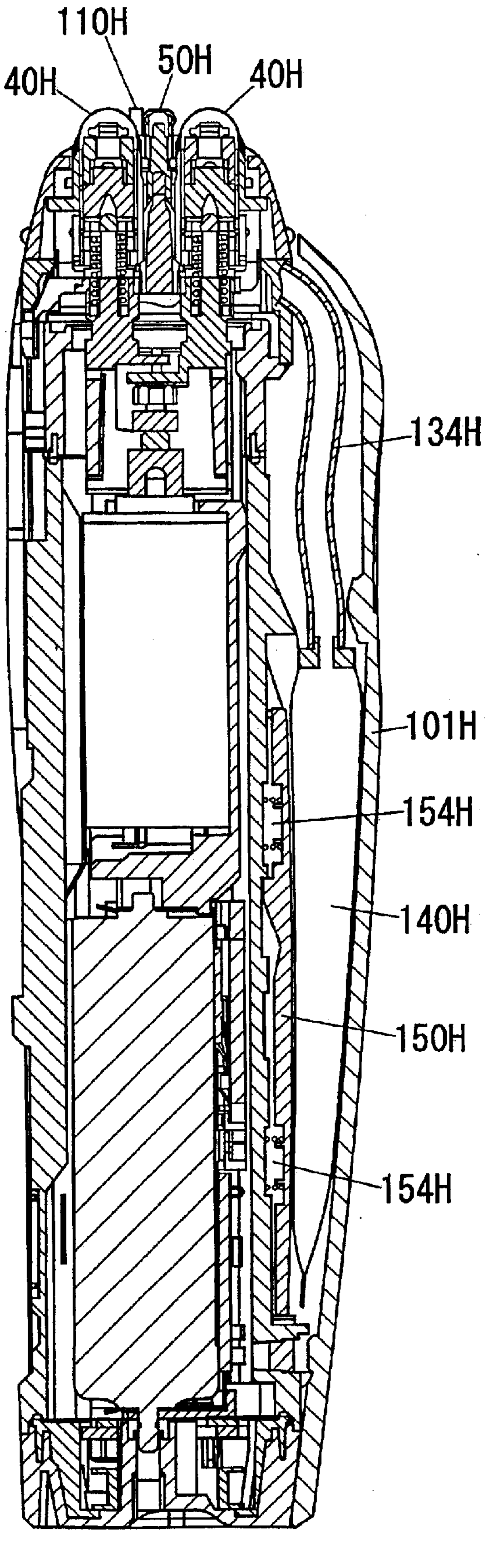
FIG. 24 is a side section of the shaver of the above embodiment.
Figure 25:
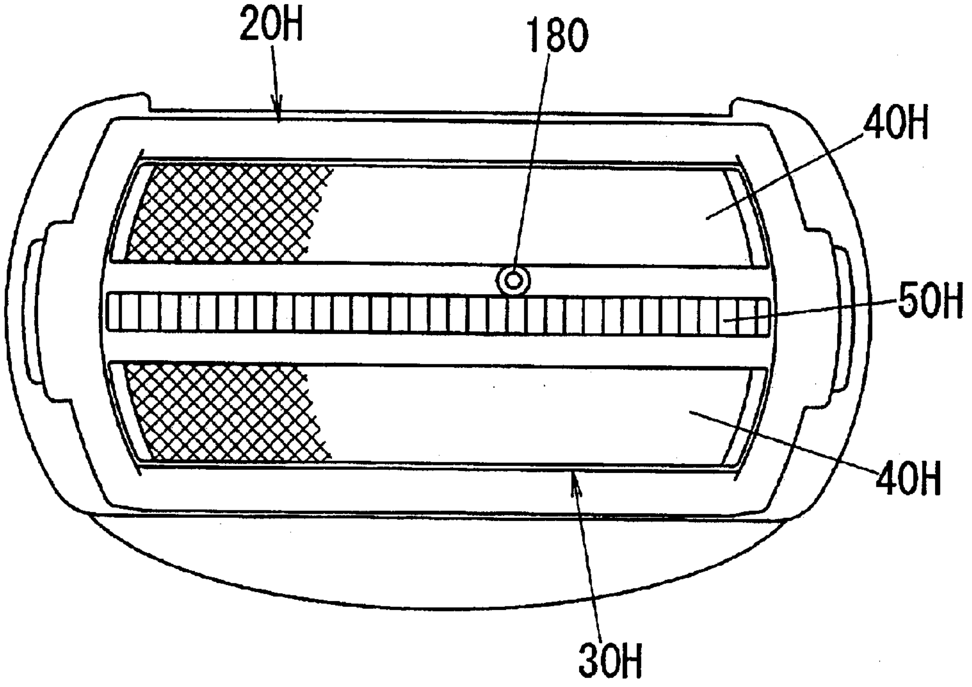
FIG. 25 is a top view of the above shaver.

Third Embodiment <FIGS. 23 to 25>

Referring to FIGS. 23 to 25, there is shown a hair removing device in accordance with a third embodiment of the present invention which is identical in structure to the first embodiment except that an applicator 110H is incorporated into a shaving unit 30H and that a diaphragm pump 160H is disposed just below the shaving unit. Thus, the shaving unit 30H assumes an appearance of a treatment head 20H. The structures and operation of the shaving unit 30H are identical to those in the first embodiment. Therefore, no duplicate explanation is made herein. Like parts are designated by like reference numerals with a suffix letter of "H". The pump 160H is mounted on top of the housing 10H with its inlet connected to a tank 140H by means of the flexible tube 134H and with its outlet connected to an upright extending duct 166. The pump 160H has a diaphragm 170 with a lever 172 which is held in an abuttable relation with a cassette 44 carrying the shearing foils of the short-hair cutters 40H as well as the long-hair cutter 50H. When the cassette 44 is depressed as a result of the short-hair cutter and/or the long-hair cutter, i.e., the shaving unit 30H being pressed against the user's skin, as shown in FIG. 23B, the cassette 44 pushes the lever 172 to deform the diaphragm 170 in a direction of delivering the lotion from within the pump to the duct 166 while opening an outlet valve 164H. When the cassette 44 returns upwardly by the action of the bias springs as a result of the shaving unit 30H being released from the user's skin, as shown in FIG. 23A, the diaphragm 170 returns by its own resiliency to draw the lotion from the tank into the pump while opening the inlet valve 162H. In this sense, the shaving unit 30H itself constitutes the actuator which activates the pump upon seeing the shaving unit being held in the operable relation with the user'skin.

The applicator 110H includes a lotion dispensing pipe 180 which is floatingly connected to the duct 166 by means of a spring 181 to have its upper end exposed between the long-hair cutter 50H and one of the short-hair cutters 40H, as shown in FIG. 25. The upper end of the pipe 180 is normally held in level with the top of the shaving unit 30H such that the pipe can be depressed together with the short-hair cutter or the long-hair cutter. Thus, the lotion is fed to the user's skin out of the pipe 180 in synchronous with the shaving unit being pressed against the user's skin. As shown in FIG. 24, the tank 140H is mounted on a shell 101H detachable to the housing 10H for replacement of the tank or refilling of the lotion. The tank 140H may be compressed by a pressurizer 150H with springs 154H for giving additional force of supplying the lotion from the tank to the pump.

Figure 26A:
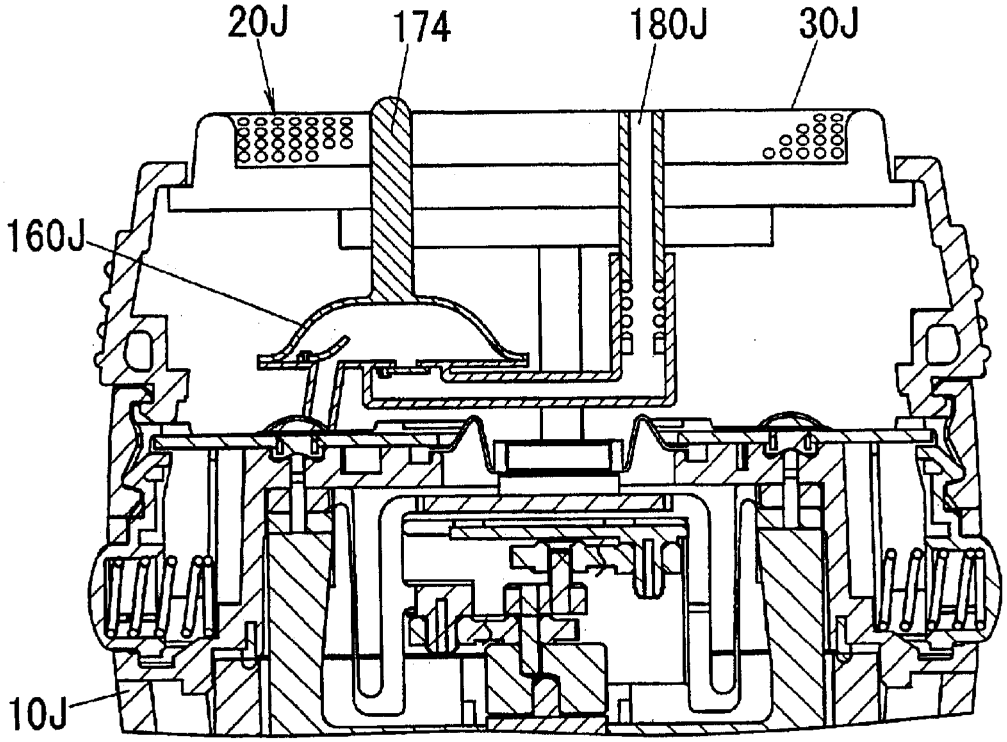
FIGS. 26A and 26B are front sections respectively of a shaver in accordance with a modification of the third embodiment.
Figure 26B:
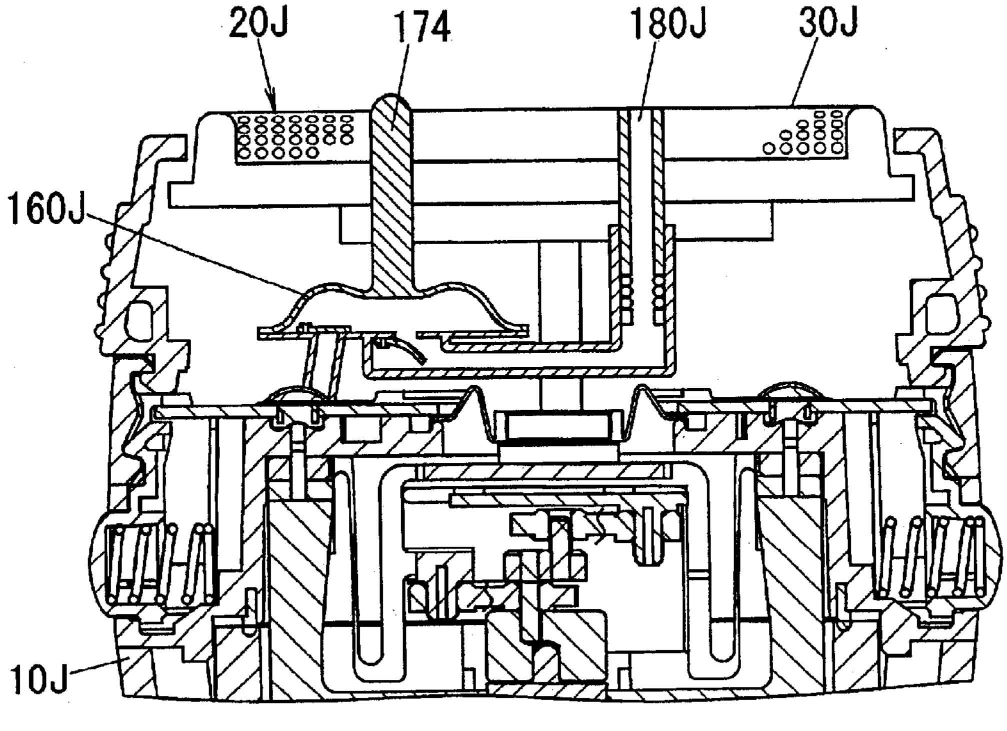
Figure 27:
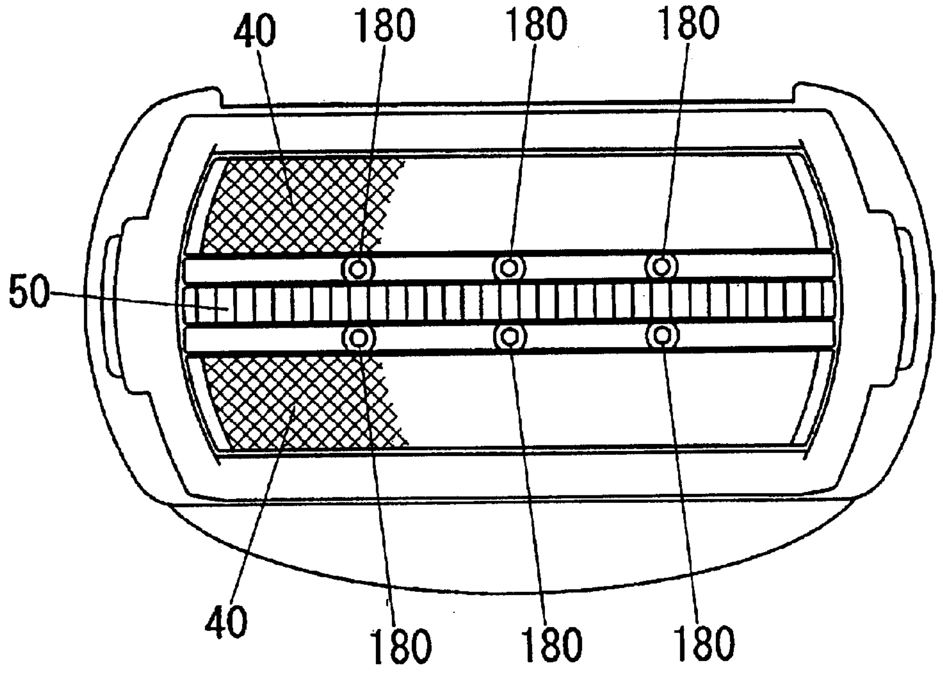
FIG. 27 is a top view of the shaver of the above embodiment.
Figure 28:
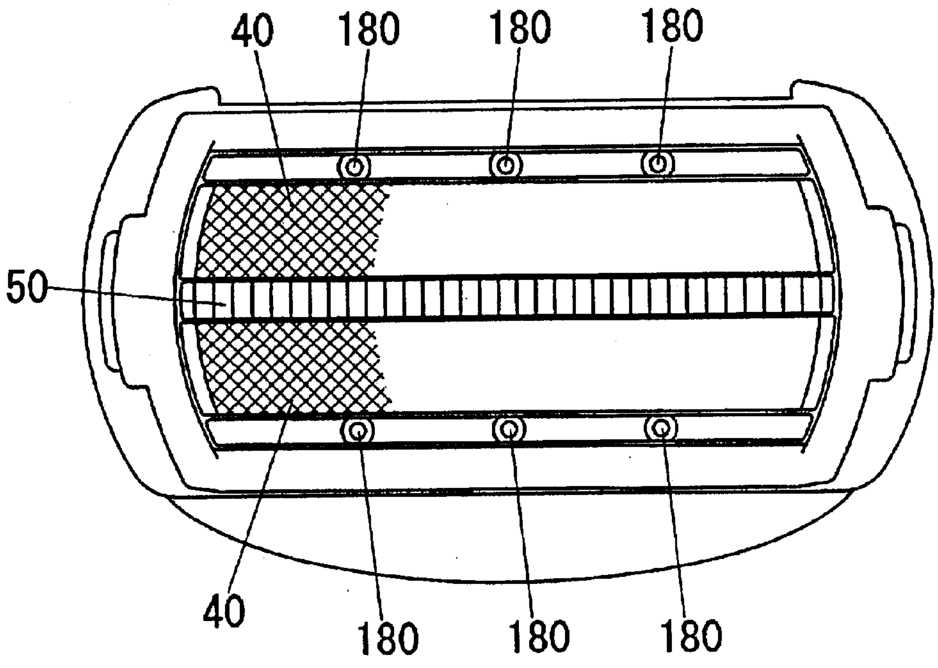
FIG. 28 is a top view of a shaver in accordance with another modification of the above embodiment.

FIGS. 26A and 26B shows a modification of the above embodiment in which the pump 160J is activated by the use of a plunger 174 extending from the diaphragm upwardly through the shaving unit 30J, instead of using the movement of the cassette of the shaving unit. Like parts are designated by like reference numerals with a suffix letter of "J". Although the embodiment and the modification of FIGS. 23 to 26 illustrate only one lotion dispensing pipe, it is equally possible to provide a multiplicity of lotion dispensing pipes, as shown in FIGS. 27 and 28, either with the pipes 180 being arranged between the long-hair cutter 50 and the short-hair cutters 40 or with the pipes 180 outwardly of the short-hair cutters 40 away from the long-hair cutter 50. In this connection, the duct 166 is configured in the form of a manifold for floating connection to the multiplicity of the pipes.

Figure 29A:
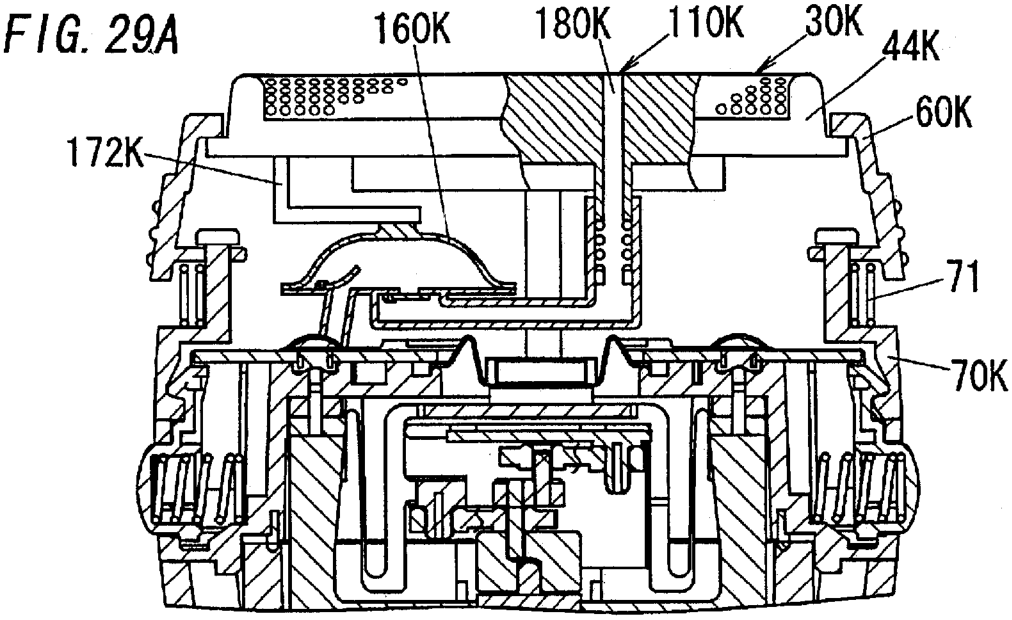
FIGS. 29A to 29C are front sections and top view respectively of a shaver in accordance with a further modification of the third embodiment.
Figure 29B:
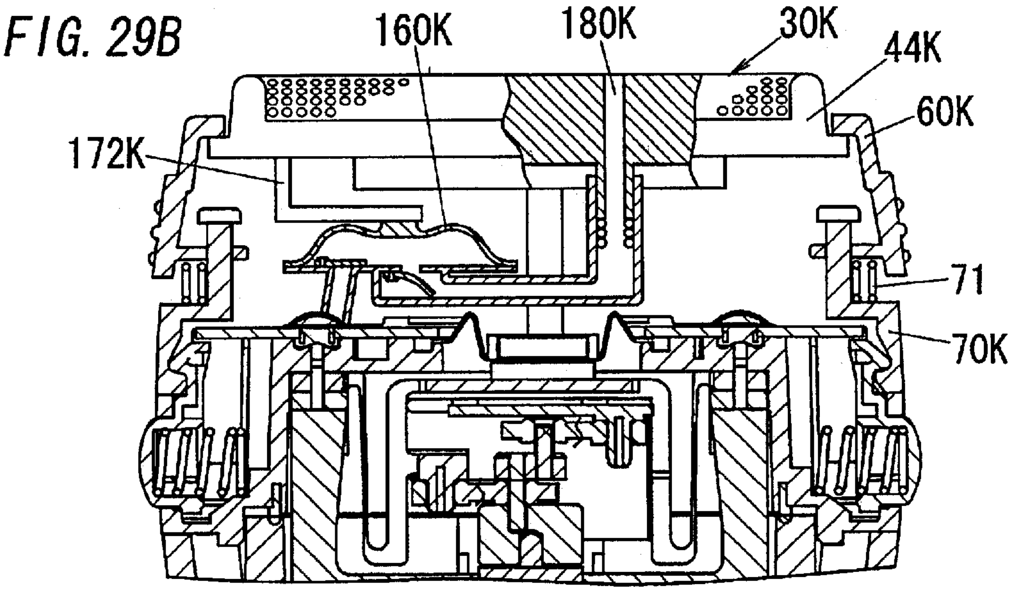
Figure 29C:
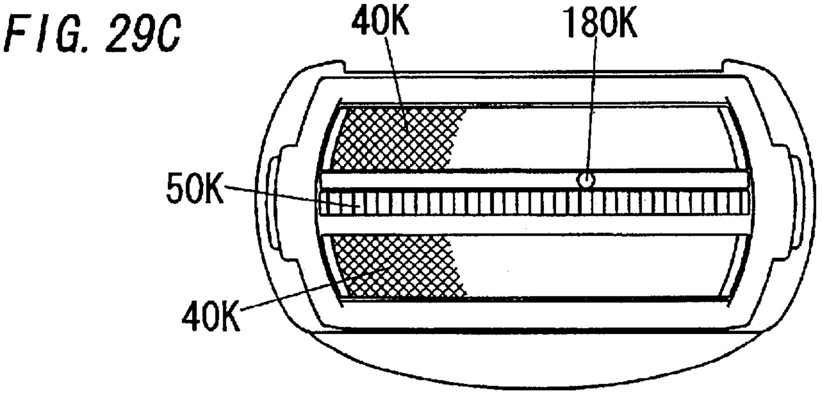

FIGS. 29A and 29C show a further modification of the device in which the top frame 60K mounting the shearing foils of the short-hair cutters 40K and the long-hair cutter 50K is floatingly supported to the base frame 70K by means of springs 71. In this modification, therefore, the pump 160K can be activated to dispense the lotion also in response to the downward movement of the top frame 70K relative to the housing 10K. Like parts are designated by like reference numerals with a suffix letter of "K". The lever 172K extending from the diaphragm 170K is kept in contact with the cassette 44K holding the shearing foils of the short-hair cutters and supported to the top frame 60K such that the pump is activated to deliver the lotion from the pump to the user's skin through the pipe 180K either when the short-hair cutter 40K is depressed or when the top frame 60K is depressed by contact with the skin, as shown in FIG. 29B. As the shaving unit 30K is released from the user's skin, the top frame 60K returns by the action of the springs 71 to the position of FIG. 29A, thereby drawing the lotion from the tank to be ready for applying the lotion in the next operation of depressing the shaving unit 30K. Although the illustrated modification shows only one pipe 180K exposed between the long-hair cutter 50K and one of the short-hair cutters 40K, it is equally possible to provide a multiplicity of the pipes as explained with reference to FIGS. 27 and 28.

Figure 30A:
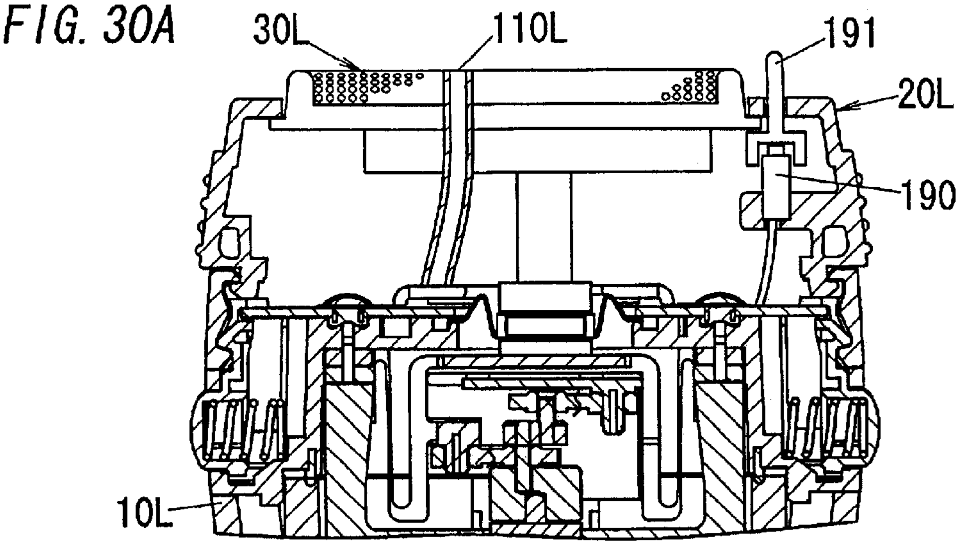
FIGS. 30A and 30B are a front section and a side section respectively of a shaver in accordance with a fourth embodiment of the present invention.
Figure 30B:
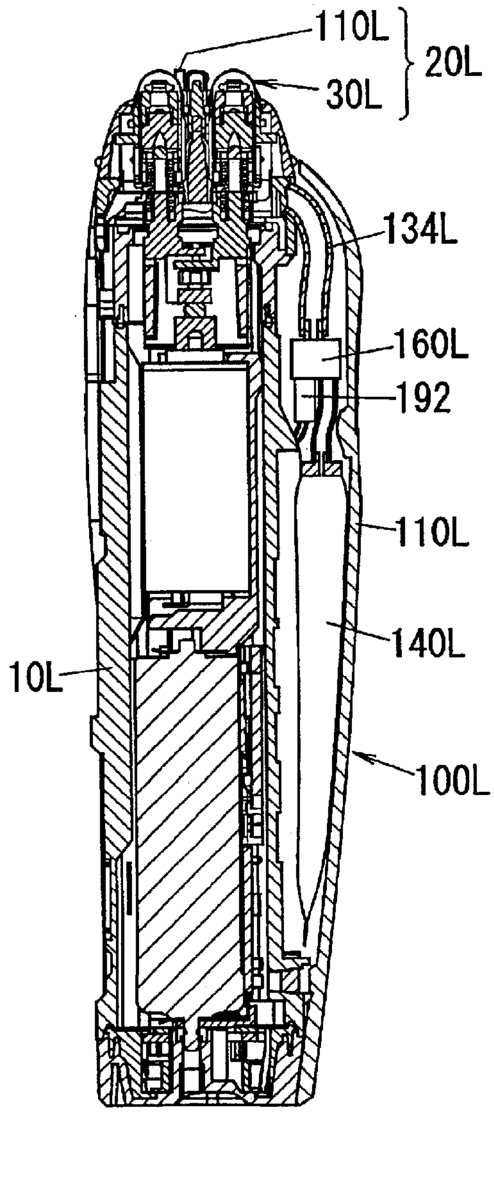

Fourth Embodiment <FIGS. 30A and 30B>

FIGS. 30A and 30B show a hair removing device in accordance with a fourth embodiment of the present invention which is similar to the third embodiment except for the provision of an electrically operated pump 160L and an electric switch 190 for activating the pump. Like parts are designated by like reference numerals with a suffix letter of "L". The applicator 110L is in the form of a lotion dispensing pipe incorporated in the shaver unit 30L and is connected through the pump to the tank 140L on the front face of the housing 10L. The pump 160L and the tank 140L are integrated into a lotion feeding module 100L detachable to the housing. That is, the module 100L includes a shell 101L mounting the pump and the tank. The pipe 110L is connected to a flexible tube 134L extending from the shaver unit 30L into the module 100L for detachable connection with the pump, as shown in FIG. 30B. The switch 190 is supported on a suitable member fixed to the housing 10L and is turned on and off by means of a switch knob 191 projecting on top of the treatment head 20L in a closely adjacent relation to the shaving unit 30L such that when the shaving unit 30L is held into operable relation to the user's skin, the switch knob 191 comes into contact with the user's skin, thereby turning on the switch 190 and activating the pump 160L to feed the lotion continuously or intermittently for a predetermined time period. In this sense, the switch knob 191 defines an actuator which senses the contact with the user's skin and activating the pump for feeding the lotion from the tank. The pump 160L is preferably a diaphragm pump and is driven by a motor 192 which is energized by a battery 16 incorporated in the housing for driving the inner cutters of the shaving unit 30L.

Figure 31:
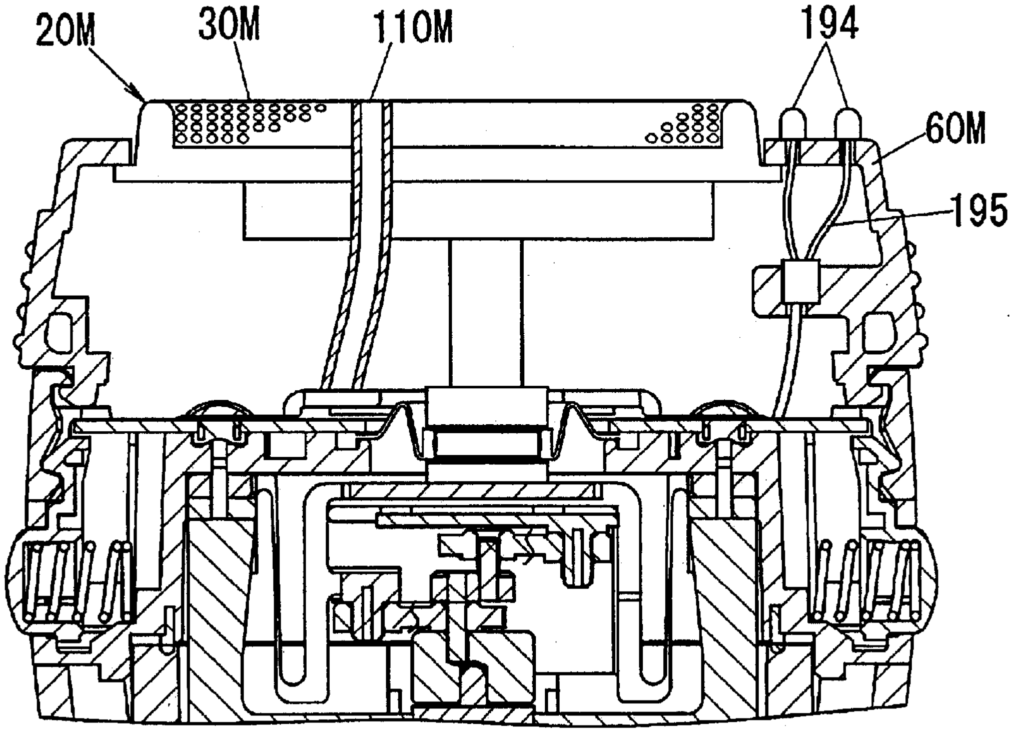
FIG. 31 is a vertical section of a shaver in accordance with a modification of the fourth embodiment.
Figure 32A:
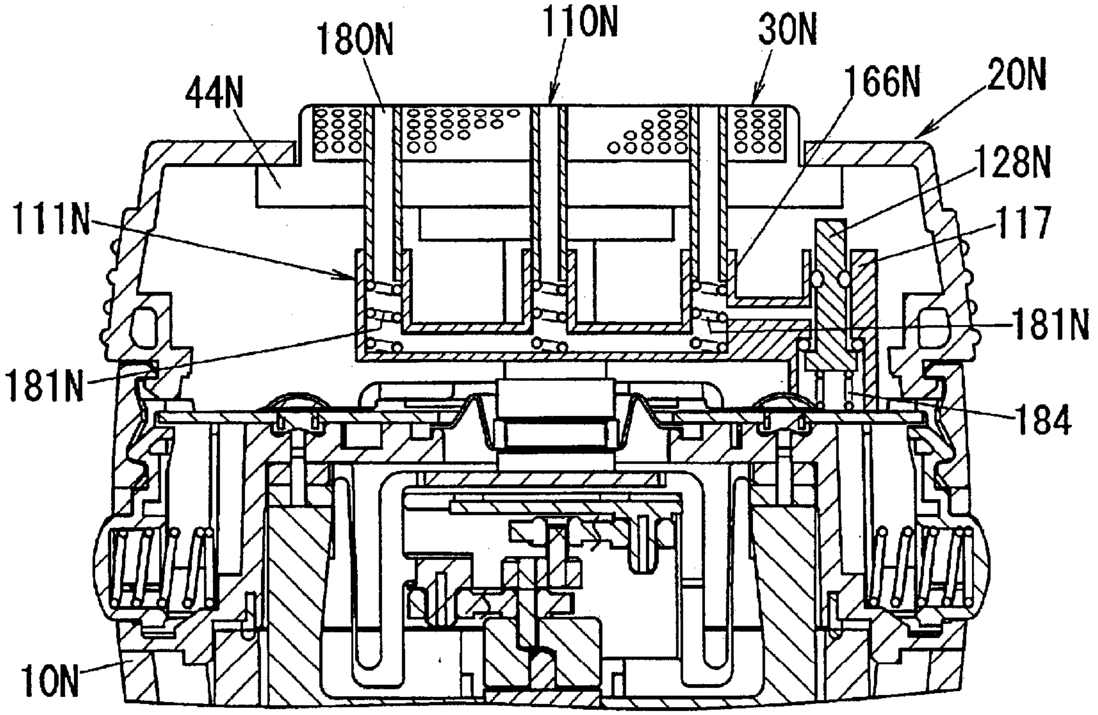
FIGS. 32A and 32B are front sections respectively of a shaver in accordance with a fifth embodiment of the present invention.
Figure 32B:
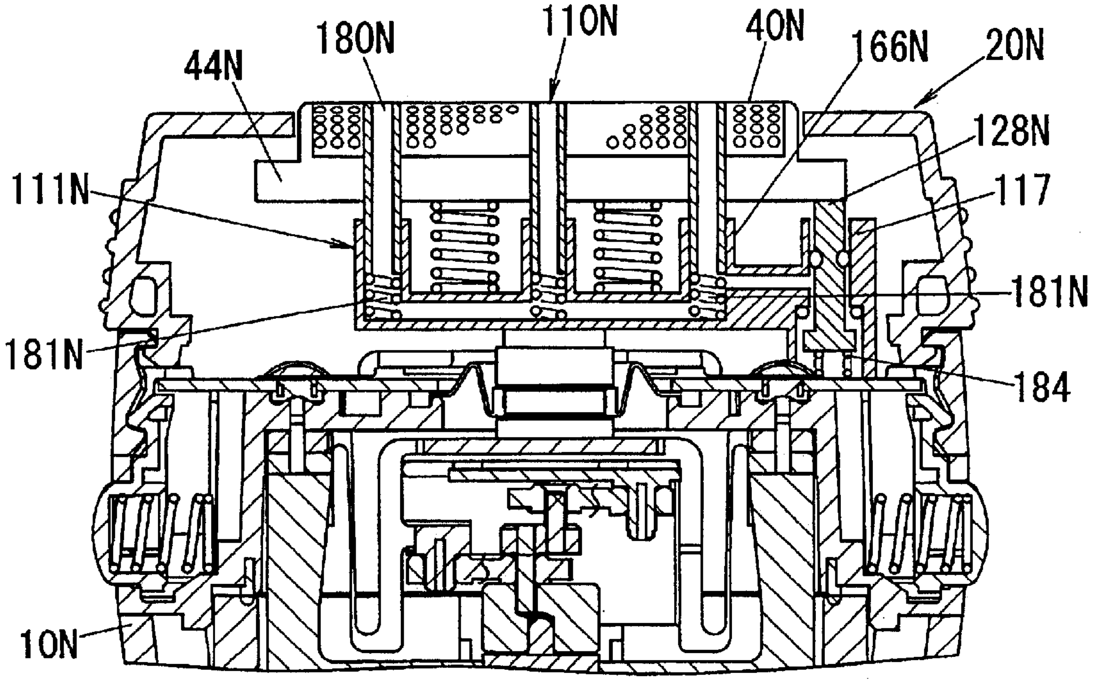

Instead of using the switch knob, it is possible to use moisture sensors 194 which acknowledge the skin contact and actuate the pump when sensing a certain amount of moisture inherent to the user's skin. As shown in FIG. 31, the moisture sensors 194 projects on the top frame 60M and connected to the motor of the pump through leads 195. Like parts are designated by like numerals with a suffix letter of "M".

Fifth Embodiment <FIGS. 32 to 35>

Figure 33:
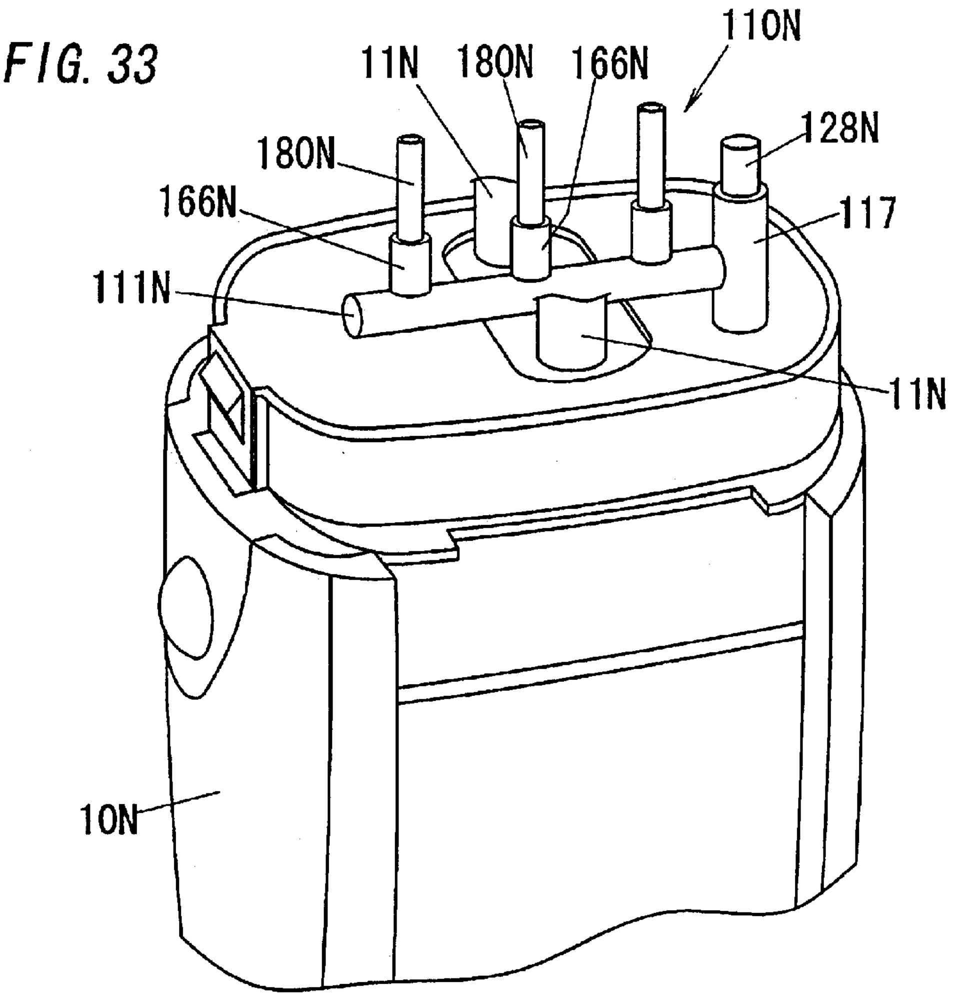
FIG. 33 is a perspective view of the above shaver shown with a hair removing unit removed.
Figure 34:
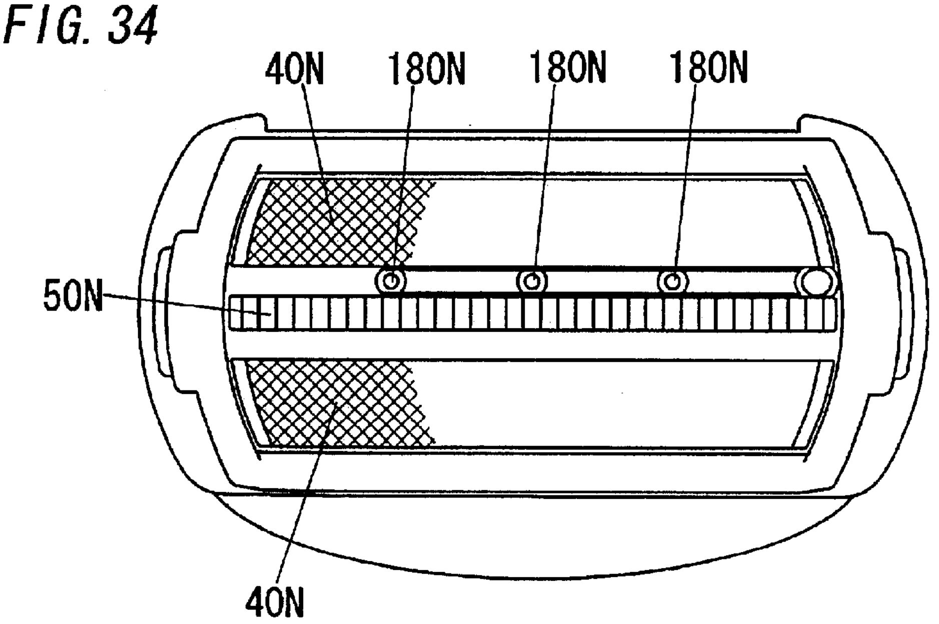
FIG. 34 is a top view of the above shaver.

Referring to FIGS. 32 to 35, there is shown a hair removing device in accordance with a fifth embodiment of the present invention which is similar to the previous embodiment in that the applicator 110N is incorporated in the shaver unit 30N assuming the appearance of the treatment head 20N, but shows a different structure of the applicator. Like parts are designated by like reference numerals with a suffix letter of "N". The applicator 110N has a header 111N connected to be supplied with the lotion from the tank 140N and a plurality of lotion dispensing pipes 180N for dispensing the lotion from the header over the user's skin, as best shown in FIG. 33. The header 111N is secured on top of the housing 10N and includes upright ducts 166N each fitted with a spring 181N. Each of the pipes 180N extends upright between the long-hair cutter 50N and the short-hair cutter 40N, as shown in FIG. 34, to have its upper end in level with the upper ends thereof. The lower end of each pipe 180N is fitted into each duct 166N and is floatingly supported by means of the spring 181N such that the pipe can be depressed together with the long-hair cutter and the short-hair cutters. The header 111N has an inlet 117 which is connected to the tank 140N by means of the flexible tube 134N and is provided with a stop valve 128N which is biased by a spring 184 to normally close a flow path from the tank to the header. The stop valve 128N has its upper end projecting upwardly in an abuttable relation with the cassette 44N carrying the shearing foil of the short-hair cutter 40N. When the short-hair cutter 40N is depressed in response to being pressed against the user's skin, as shown in FIG. 32B, the cassette 44 pushes the stop valve 128N against the bias of spring 184 to open the flow path, thereby allowing the lotion to be supplied from the tank 140N to the header 111N and therefore dispensing the lotion from the pipes over the user's skin. As soon as the short-hair cutter, i.e., the shaving unit 30N is released from the user's skin, as shown in FIG. 32A, the stop valve 128N returns to close the flow path, ceasing the lotion supply from the tank to the header and therefore the lotion feeding from the applicator.

Figure 35A:
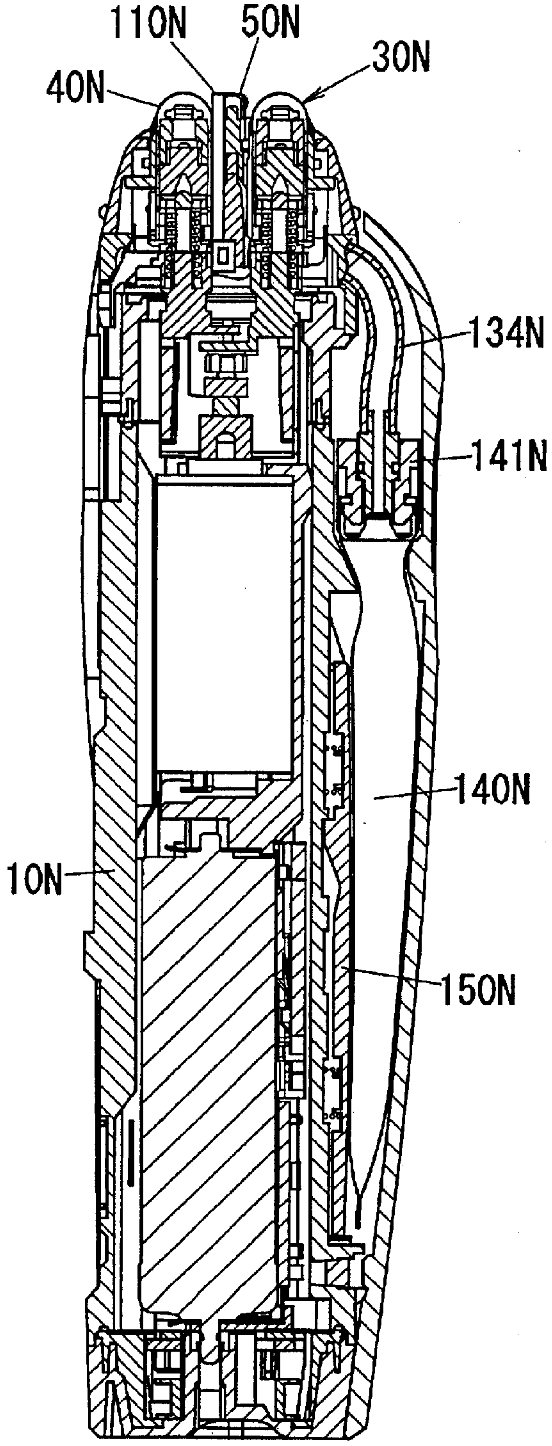
FIGS. 35A and 35B are side sections respectively of the above shaver.
Figure 35B:
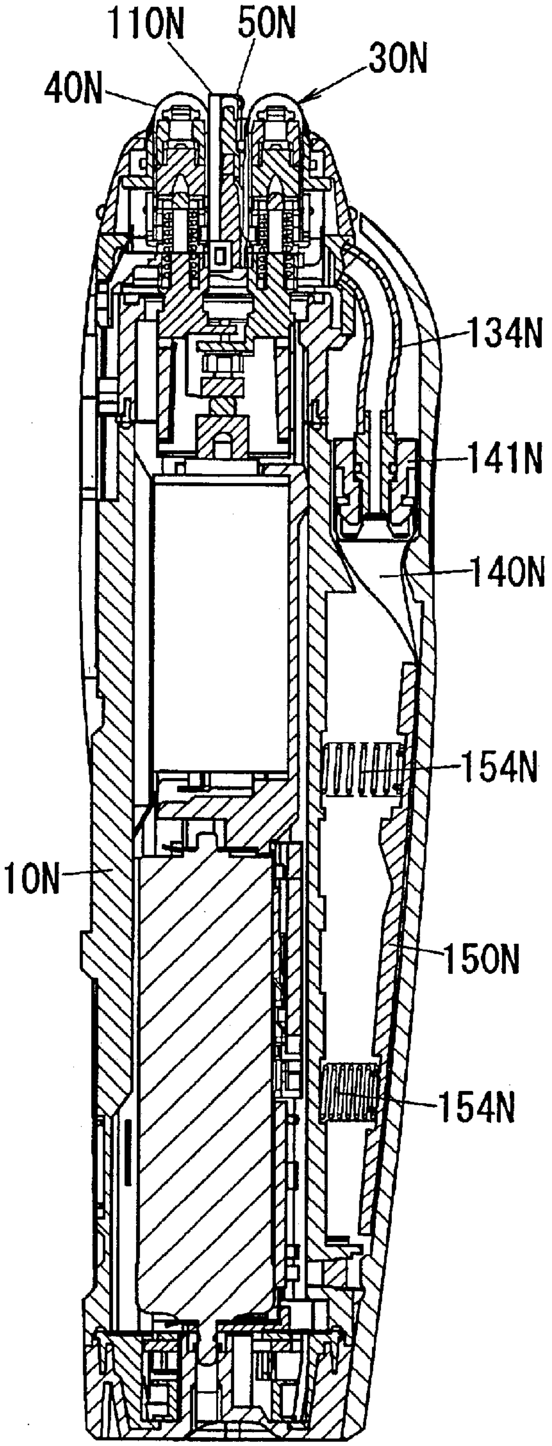

As shown in FIGS. 35A and 35B, the tank 140N is held on a shell 101N detachable to the housing 10N, and is compressed by a like pressurizer 150N to give a positive pressure for supplying the lotion from the tank to the header 111N. The pressurizer 150N is urged by springs 154N against the tank 140N so as to squeeze the lotion out of the tank even when it becomes nearly empty, as shown in FIG. 35B. The tank 140N has the mouth 141N detachable to the flexible tube 134N extending from the header 111N.

Figure 36:
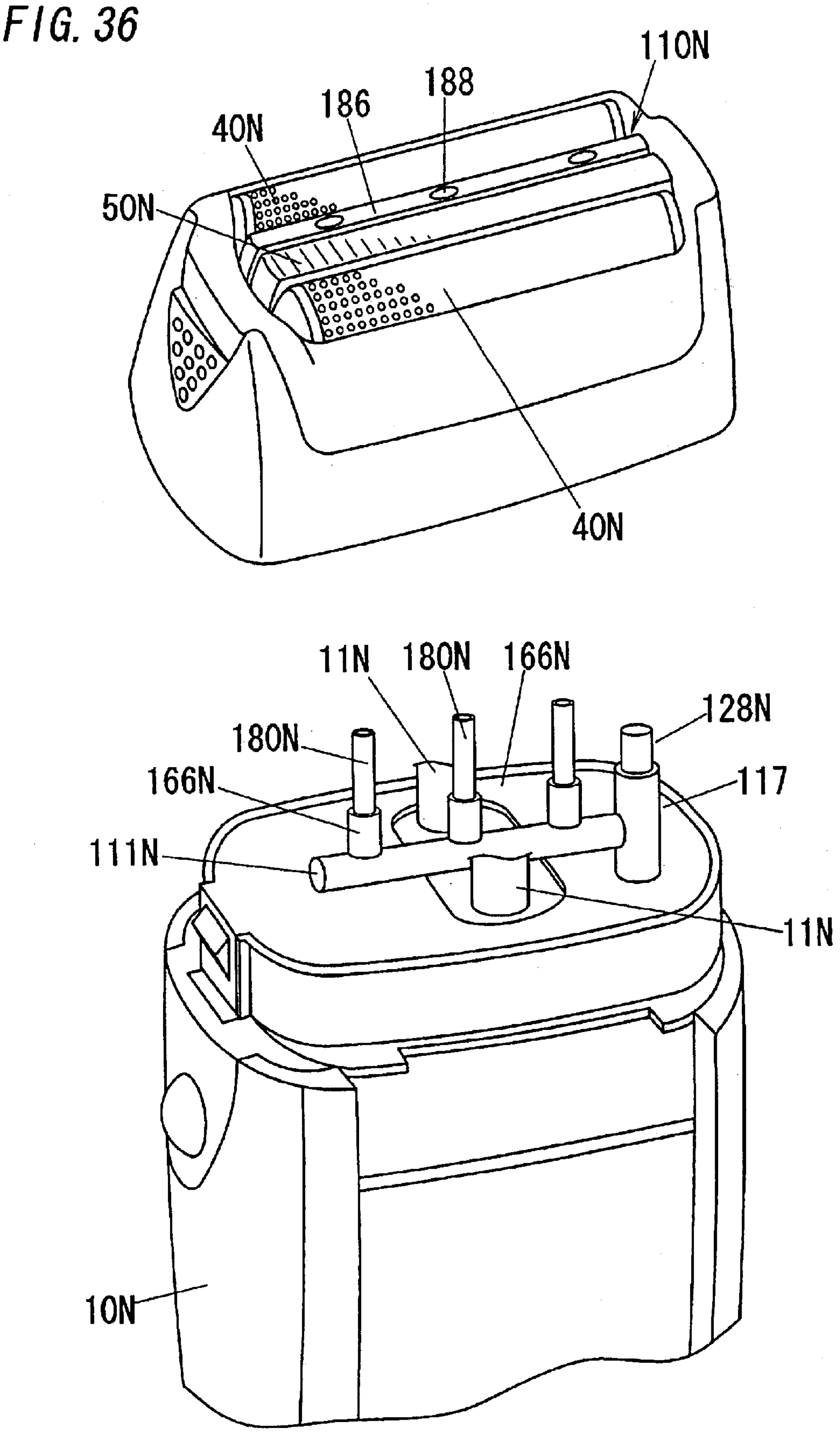
FIG. 36 is an exploded perspective view of a shaver in accordance with a modification of the above embodiment.

As shown in FIG. 36, the applicator 110N may includes a bar 186 which holds the pipes 180N together and which is floatingly supported to the top frame 60N to be capable of being depressed together with the short-hair cutters 40N and the long-hair cutter 50N. For this purpose, the bar 186 is formed with holes 188 each detachably receiving the upper end of each pipe 180N. In this modification, the stop valve 128N is held in the abuttable relation with the lower end of the bar other than the cassette holding the shearing foil of the short-hair cutter. The bar 186 defines the actuator which acknowledges the event of the shaving unit being depressed and activates the stop valve 128N to open for supplying the lotion from the tank to the header of the applicator.

Figure 37:
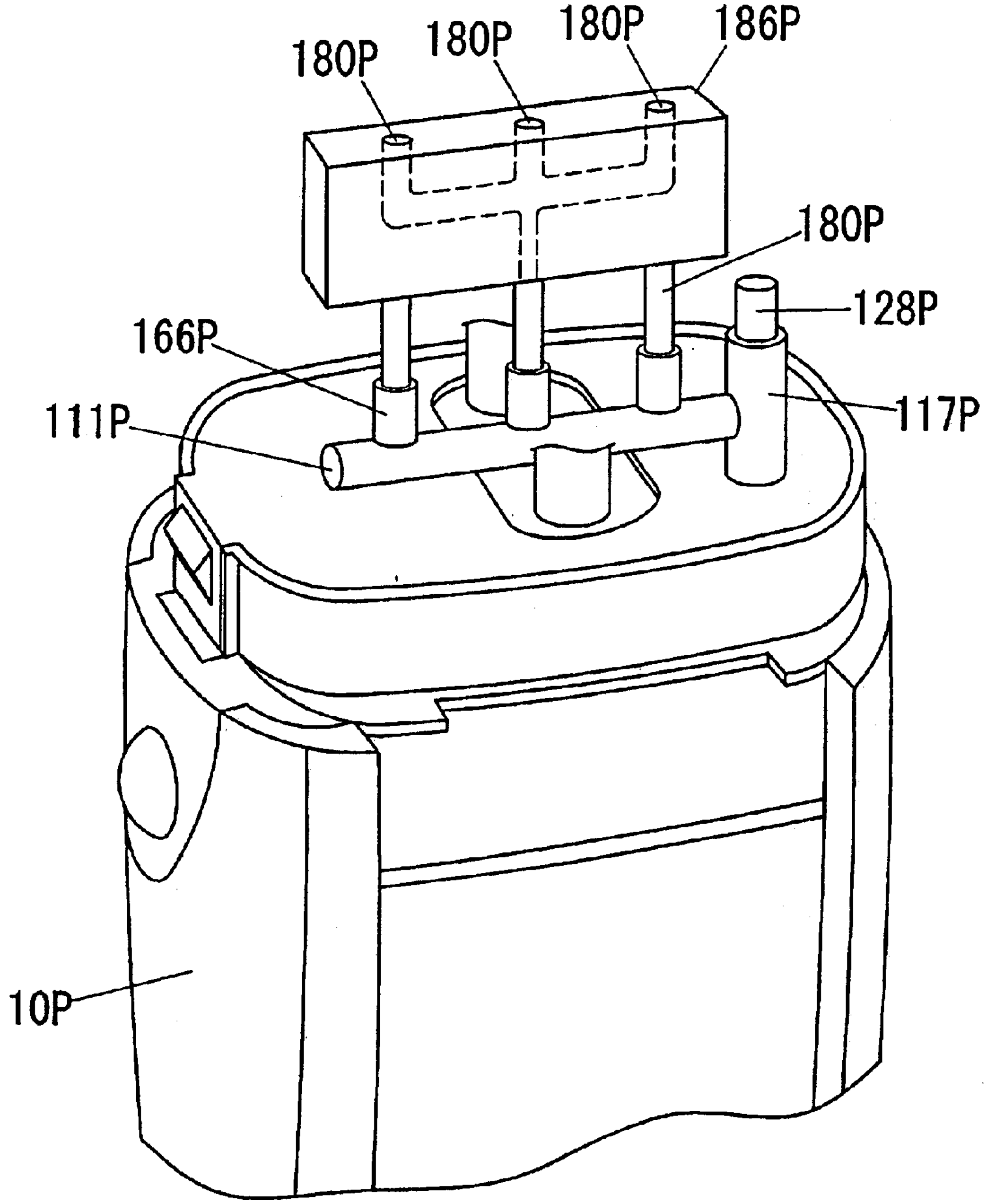
FIG. 37 is a perspective view of a shaver in accordance with another modification of the above embodiment.

FIG. 37 shows another modification of the applicator 110P which includes a like bar 186P holding the pipes 180P together and is movable together with the pipes. The other structures are identical to those of the fifth embodiment. Therefore, like parts are designated by like reference numerals with a suffix letter of "P".

Instead of using the pressurizer for supplying the lotion to the applicator, it is equally possible to use a diaphragm pump as is described with reference to the fourth embodiment. In this modification, the diaphragm pump is interlocked with the stop valve 128P so as to be activated each time the stop valve is opened in response to the shaving unit being pressed against the user's face.

The present invention should be interpreted in terms of not only to the above embodiments and their modifications but also to any combination of the features made herein.

This application is based upon and claims the priority of Japanese Patent Application No. 2001-133082, filed in Japan on Apr. 27, 2001 and No. 2001-180805, filed in Japan on Jun. 14, 2001, the entire contents of which are expressly incorporated by reference herein.

What is claimed is:

1. A hair removing device with a lotion feeder, said device comprising:

a housing;

a treatment head mounted to said housing and including a hair removing unit which is held against a user's skin for hair depilation or hair epilation, said treatment head also including an applicator which dispenses a lotion on the user's skin;

a tank holding the lotion;

a lotion supply mechanism for supplying said lotion from said tank to said applicator, wherein said treatment head is provided with an actuator which acknowledges an event of said treatment head coming into an operative condition with the skin, said actuator activating said lotion supply mechanism to supply said lotion from said tank to said applicator, said actuator is included in said applicator in a skin-contact relation with the skin, said actuator being movable relative to said housing so as to activate said lotion supply mechanism when it is depressed as a result of said applicator being pressed against the user's skin, said applicator is floatingly supported to said housing so as to be depressed when it is pressed against the user's skin, said hair removing unit has an upright axis and has an overall section which is wider toward its bottom than at its top end with respect to said upright axis, said applicator being movable relative to said housing between a projected position where said applicator has its top end close to the top end of the hair removing unit and a retracted position where said applicator has its top end lowered from the top end of the hair removing unit, said applicator having a longitudinal axis which is inclined at a first angle with respect to the upright axis of said hair removing unit so as to bring the top end of the applicator close to the top end of said hair removing unit when said applicator is in the projected position, and which is inclined at a second angle different from said first angle with respect to the upright axis of the hair removing unit so as to avoid the applicator from interfering with the bottom of the hair removing unit when said applicator is in the retracted position.

2. A hair removing device with a lotion feeder, said device comprising:

a housing;

a treatment head mounted to said housing and including a hair removing unit which is held against a user's skin for hair depilation or hair epilation, said treatment head also including an applicator which dispenses a lotion on the user's skin;

a tank holding the lotion;

a lotion supply mechanism for supplying said lotion from said tank to said applicator, wherein said treatment head is provided with an actuator which acknowledges an event of said treatment head coming into an operative condition with the skin, said actuator activating said lotion supply mechanism to supply said lotion from said tank to said applicator, said actuator is movable relative to said housing between a non-depressed position and a depressed position where the actuator is depressed towards said housing against a bias, said lotion supply mechanism including a pump having a pump chamber for temporarily storing said lotion supplied from said tank, said pump having an inlet flap valve permitting said lotion to be fed into said pump chamber from said tank and an outlet flap valve permitting said lotion to be delivered from said pump chamber to said applicator, said actuator being interlocked with said pump such that only said outlet flap vale is caused to open for feeding said lotion to said applicator from said pump chamber in response to said actuator being depressed to said depressed position and that only said inlet flap valve is caused to open for drawing said lotion into said pump chamber from said tank in response to said actuator returning to said non-depressed position, said pump chamber is surrounded by a stationary wall member with said inlet flap valve and a movable wall member with said outlet flap valve, said movable wall member being movable relative to said stationary wall member, and said movable wall member being interlocked with said actuator so as to generate a positive pressure within said pump chamber for feeding said lotion to said applicator through said outlet flap valve when said movable wall member moves towards said stationary wall member in response to said actuator moving to said depressed position and to generate a negative pressure within said pump chamber for drawing said lotion into said pump chamber through said inlet flap valve when said movable wall member moves away from said stationary wall member in response to said actuator returning to said non-depressed position.

3. The device as set forth in claim 2, wherein said actuator is included in said applicator in the form of a skin guide for contact with the user's skin, said skin guide including at least one aperture communicating with said pump chamber through said outlet flap valve for dispensing said lotion over the user's skin.

4. The device as set forth in claim 2, wherein said movable wall member is configured as a skin guide for contact with the user's skin, said skin guide defining said actuator and also said applicator, said skin guide being provided with a projection around said outlet flap valve in order to protect said outlet flap valve from interfering with the use's skin.

* * * * *